United States Patent
Takashi et al.

(10) Patent No.: US 8,030,561 B2
(45) Date of Patent: Oct. 4, 2011

(54) RICE PLANT AND METHOD FOR PRODUCING THE SAME

(75) Inventors: Tomonori Takashi, Wako (JP); Asuka Nishimura, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 567 days.

(21) Appl. No.: 12/122,389

(22) Filed: May 16, 2008

(65) Prior Publication Data

US 2008/0320611 A1 Dec. 25, 2008

(30) Foreign Application Priority Data

May 17, 2007 (JP) ................................. 2007-131987

(51) Int. Cl.
- *A01H 1/00* (2006.01)
- *A01H 1/02* (2006.01)
- *A01H 5/00* (2006.01)
- *A01H 5/10* (2006.01)

(52) U.S. Cl. ..................... 800/320.2; 800/260; 800/278; 800/298; 800/267; 435/468

(58) Field of Classification Search ........................ None
See application file for complete search history.

(56) References Cited

U.S. PATENT DOCUMENTS

| | | |
|---|---|---|
| 2004/0250315 A1 | 12/2004 | Okawa et al. |
| 2007/0186302 A1* | 8/2007 | Ashikari et al. ............ 800/278 |

FOREIGN PATENT DOCUMENTS

| | | |
|---|---|---|
| JP | 2003-260 A | 1/2003 |
| JP | 2004065251 A | 3/2004 |
| WO | 2004066719 A1 | 8/2004 |

OTHER PUBLICATIONS

Yamamoto et al. Breeding Science (2001), 51:63-71.*
Ken Ishimaru et al., "Improvement in Lodging Resistance of Koshihikari", Agriculture and Horticulture, 2007, pp. 365-368, vol. 82, No. 3.
Masahiro Yano et al., "Genetic Control of Flowering Time in Rice, a Short-Day Plant", Plant Physiology, Dec. 2001, pp. 1425-1429, vol. 127.

* cited by examiner

*Primary Examiner* — Medina A Ibrahim
(74) *Attorney, Agent, or Firm* — The Webb Law Firm

(57) ABSTRACT

The rice plant according to the present invention is a rice plant obtained by crossing the rice plant varieties "Koshihikari" with "Kasalath" and having improvement in both lodging resistance and decorticated grain size, wherein said rice plant has on the chromosome any one of base sequences selected from the groups consisting of: (i) a base sequence of SEQ ID NO: 1, (ii) a base sequence having at least 80% identity with the base sequence of (i) above, and (iii) the base sequence of (i) above, in which one or several bases have been deleted, substituted, inserted or added, and wherein the remaining region of the chromosome is composed of chromosomes derived from Koshihikari. According to the present invention is to provide a new rice plant which maintains the good eating quality as a characteristic of Koshihikari and has excellent lodging resistance and large grains is provided.

6 Claims, 16 Drawing Sheets

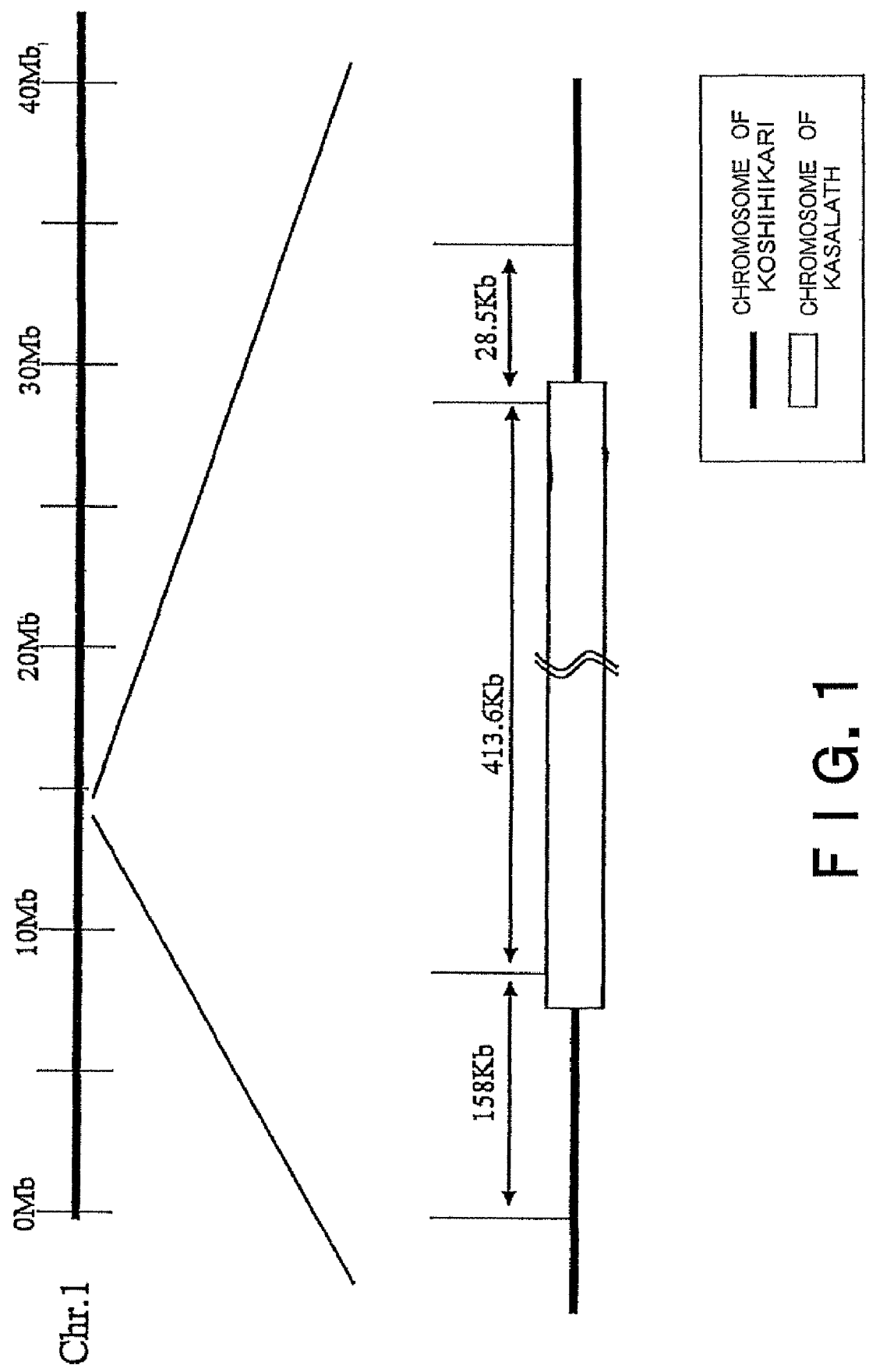
F I G. 1

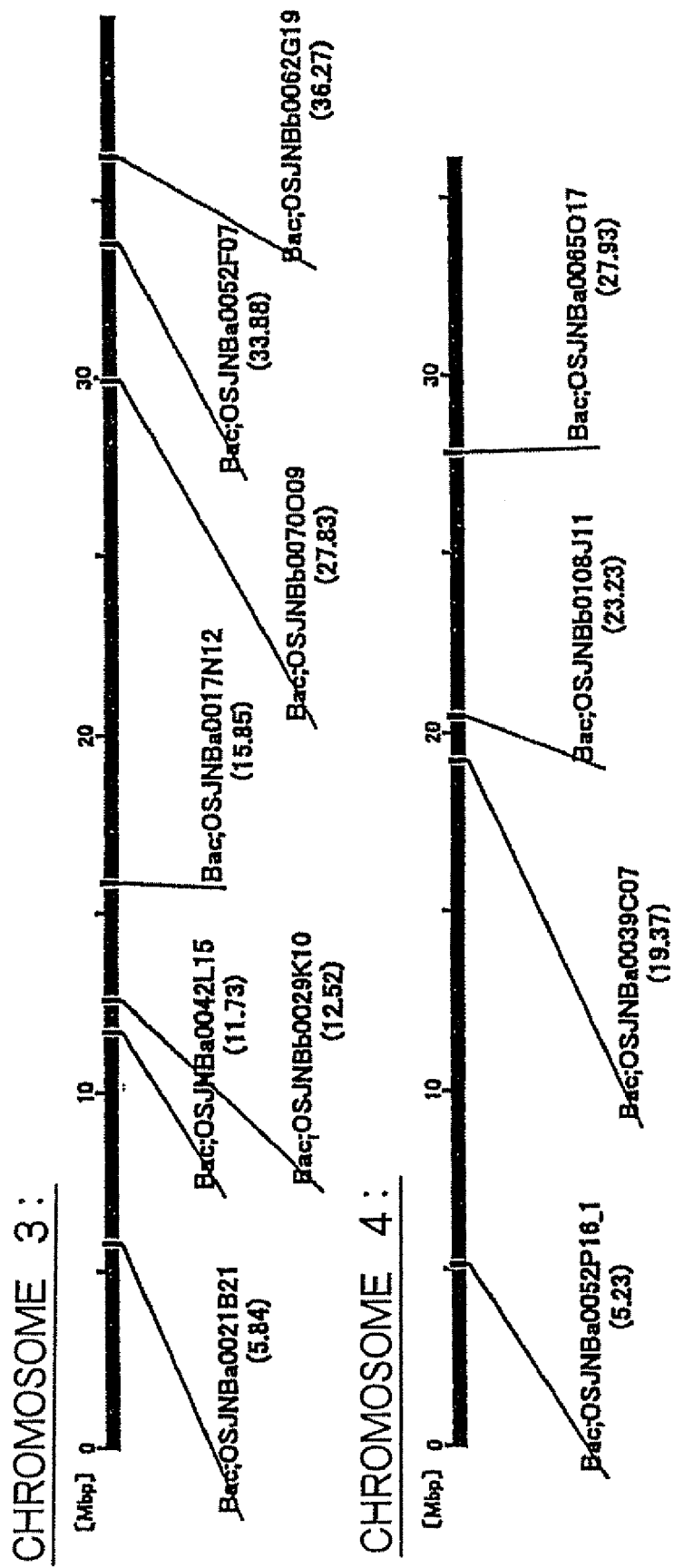
F I G. 3B

COLUMN 1 : COMPARATIVE EXAMPLE (AKIHIKARI)
COLUMN 2 : COMPARATIVE EXAMPLE (NIPPONBARE)
COLUMN 3 : COMPARATIVE EXAMPLE (KOSHIHIKARI)
COLUMN 4 : THE PRESENT INVENTION

SEQUENCE LISTING

```
<160> NUMBER OF SEQ ID NOS: 47

<210> SEQ ID NO 1
<211> LENGTH: 12161
<212> TYPE: DNA
<213> ORGANISM: Oryza sativa
<220> FEATURE:
<221> NAME/KEY: misc_feature
<222> LOCATION: (4429)..(4429)
<223> OTHER INFORMATION: n is a, c, g, or t
<220> FEATURE:
<221> NAME/KEY: misc_feature
<222> LOCATION: (4479)..(4479)
<223> OTHER INFORMATION: n is a, c, g, or t
<220> FEATURE:
<221> NAME/KEY: misc_feature
<222> LOCATION: (4520)..(4520)
<223> OTHER INFORMATION: n is a, c, g, or t
<220> FEATURE:
<221> NAME/KEY: misc_feature
<222> LOCATION: (4555)..(4555)
<223> OTHER INFORMATION: n is a, c, g, or t
<220> FEATURE:
<221> NAME/KEY: misc_feature
<222> LOCATION: (4561)..(4561)
<223> OTHER INFORMATION: n is a, c, g, or t
<220> FEATURE:
<221> NAME/KEY: misc_feature
<222> LOCATION: (4563)..(4563)
<223> OTHER INFORMATION: n is a, c, g, or t
<220> FEATURE:
<221> NAME/KEY: misc_feature
<222> LOCATION: (4577)..(4578)
<223> OTHER INFORMATION: n is a, c, g, or t
<220> FEATURE:
<221> NAME/KEY: misc_feature
<222> LOCATION: (4823)..(4823)
<223> OTHER INFORMATION: n is a, c, g, or t
<220> FEATURE:
<221> NAME/KEY: misc_feature
<222> LOCATION: (7186)..(7186)
<223> OTHER INFORMATION: n is a, c, g, or t
<220> FEATURE:
<221> NAME/KEY: misc_feature
<222> LOCATION: (11994)..(11994)
<223> OTHER INFORMATION: n is a, c, g, or t

<400> SEQUENCE: 1
```

```
ctcgagcttt tttgactgcc ctaatcaggc gggttccttg tgggacccac ataatgcttt    60
ttttaatcgc cttcacgggc tgcatgcaaa ctatacggca tgggacttcc actactagaa   120
aaaacgggcg gtcgaaacac gttttcgcag gcaggcaaac cttccacatg tatcttaacg   180
accgtaaaaa tctccaattt tcacaggtgg accacagcac cgttttcgca ggctacattt   240
cgaatcttcc tgggtgctac agtaaaccac ctgcaaaaat actcacggcg ccaaaaaaaa   300
tttccgccag ccccgccccc tccctattca aatcacaaat cacaaattct cacaaatctc   360
atccaaaaac aaaatccaat ccaaaaatcc atacatcaac acaaagcatt ggattcaaat   420
ccacaacatc aatttacaag ttaacatcaa tcaacatgta agctttaaaa cgaaacgtcg   480
tcgtcgccgg caaactcctt tgcatgcggt gccgctgccg ccccctccc cctctgtccg    540 gatttgggag ggagggaggg aggtgtttgc cgccaccacc gccctcccct tcctcgtag    600 ggccggatct cgggagggag gagaggggag ccgcctccgc acagccatca acgtccgtgc   660
cgccgtcgcc tcgttcgcac caccgccgtt gcttcccctc ctccggccag atctaggagc   720
ggggaggaag agaggggag ccaccgccac cgtcgccccc tcgcgtccgc gccgtcgtca    780
ccgtccacgc cgccgcgtcc gtgccgccgc tgtcgctccc cctcctctgg cgaggaggga   840
gagagaggga gccgtcgcgc cgccgtcgct cccctccttc ggcgaggagg gagagagggg   900
gagggaagag ggatgagggg gaggagagtg gcgctgagag agagagagag agacgctgag   960
gagaggaaat gagtggtggg gagggtgga ggagaagata aggaggactt agatttttt   1020 ttgggtaggt atgattttg caggcggacc acataaggtt ccgcctgcga aaatcaattt   1080
tttcacgcag accacttaag aggtccgcat gcgaaaataa aggtattttt ttaggcagac   1140
ctcttaagtg gtccgcctgg aaaaattgat tttcacaagc agatgacgaa aattcaccc    1200 ggtttatatt ttcgaagatg cttcatcgac gacatcgacc gcgtcctcta tgacggcaac   1260
gaccgcgtca ccgacaacgg catcgatcac gtcatctacg atgacaacga ctgcatcaac   1320
tccgcatcac tattgtgatg actgttacat ggcgtagaag aaccaaccaa agtggtggcc   1380
tcatcgccaa cgacgtcctc tgacatatgc aagacgtccc caatggcatc ctcagacatc   1440
tacaaggtgc aagatgctaa caattacagt ttttgtcttc acactgtggc ataaatattt   1500
ttttccgcct tcggctatat tcggctacac ctacaaccac ggttactaca tgatcggctc   1560
catcaacgaa catctataac aacaatcatt gacggaaact ccagtcaaga gcgtctgtgt   1620
catcgctatc ttccatgaca ctcccgctat gactacgtga gggaatagag gagagtcaag   1680
ggacgacacg gaaggagacg taggcaccag gtggaggacc gtccatcaaa gatgcaattg   1740
atgatggtga gttgaagaag atgaagaaat aaaagatttc aaatccagtc gcaatcgttc   1800
gcttcgctcc cgttacgact gagggggaat gttagaagca tagatatatt aattggagat   1860
aagagtcata caaatataga gataagatat catcctagag atagaattct atagataaaa   1920
tagagtccta gagataaatc tactcttact tgtacccta tatataccc atgagaggat     1980 caatgcaata caccgagaat acaacaatta gatttttta cagttgtaac tatgatacgt    2040
tgtaatatgc tggatcgggg aagagcgccc gtaatcagtg ccccagagat gtaggtctcg   2100
gctgaactcc attatcaaat accgtacctc ggtgttgtca tcatgtttga atcttctatg   2160
acgtttcttt tgcattcggt tttcgatgtg acttcagggc tggttttata ataatgatta   2220
tagtgctgtg acggcaatcg gttgtgagaa ttagctattc gggtccctcc atgtgatttt   2280
cttgtgattg ggatgtatgg taatgctagg gttttaaggt gtaggattgg tgcatgagag   2340
atcatcactt cacttgtatg accttctctc cttttatatt tttttatcat tctctccttt   2400
```

```
tttttataat gctactgaac tagtggaata caggggacta atgcaaaata aaagaaaagt    2460
atcactggtc acggcataca atttagaaag tgtgtgattt aggcatagag ctgaccacga    2520 cccctttacga cttggtcgct cggtttgtta gacgatagat caaccaacaa aagctacgat   2580
acatgatgta cgtgtcagga tacaaatcct tacaaataac aacagttatt gttcgataac    2640
ttttatcagt tgtctaggct taccaatgta aatagaaga tgaaaattcc atattactgg     2700
tatcgatcaa tgctagtaac tctttgagct ttgtctaggt taaaaaaat tatggatcca     2760 ccatcacaaa aatgaaaaac accggggaaa acaaaaaacc atttaataac agcacaagac    2820
aaaatgatgt taccgtctac ccgagctcct actccgtacc agcacaacca aacgaacagt    2880
acccgccggg tcaggggcac gttcgtaaat ttccctcccg tggctggctg gctgccatct    2940
ctctcagcca gggttggtaa tttcggccgt tcggtgggt cccgatagta aatgagctcc      3000
agtcaaaacg ccctctgcct cccctcattg cgccacacgc acaccgcatc tagatccaga    3060
tcgaaaaaat cgccatctcg ccgagtcgcc agtcgccgcc tcaacgccgg tcgccgtacc    3120
gccggcgctg cacgcccccc tccaagccgt cgcccatcg ccccagccg cccggtggtg       3180 gggcagcgga tgccgagctt ggcgaggttg ccgaggacga accaggcgag gaggacgagg    3240
atcttgtcga cgagccagag cgggagccac gccatgagca cacggcgag ctcgaacgtg      3300 gacttgccga gcacctcgcc agggaggacg tggacggcgt cgcgcaccac catcgccggg    3360
agggcgctgt ggtcgcagag gtcgagcgac accaccatgc cggagttgcc gcacccgacg    3420
acgagcacct tcttgccgcg gtacgcctcg ccggacttgt agaccgcgac atgcatcacc    3480
tcgctgctat atttgttctt ggactgtgga gacttgctgt cagtgggtgt gttcagaatt    3540
gctgctgcag cttgcagcga atttgtgatg cagcagctac agcttgtatg ctgccgagt     3600 agagcgagtg ttgctatctg ttttttgttc tcttttcag aaatttcgcc cgcaaatttt      3660
aaatttgaat tcaaatttt aaagaacta gcaaatatgc ccgtgcgttg caccgggtga      3720
atatcaaaca aatattgatg ggtaagattg cttgtgtact tataacacat atgcacaaaa    3780
atattgaata tgtacatacc tcgcaaatat ctccaaattt tatacatatg agttgtgtaa    3840
atcgtgtgag ttccatattg tcatgttgat atggagtatt actgatgagc ccatctatgg    3900
tgataatttt ggaggttgta gctcaacgaa tttgtatttg ctatgtatct caacgttgat    3960
aagtcactac cacaaccatc ggcgaccttt ctcgggatcc aagcatgttg accccgccaa    4020
cgtggcgtcg gtgcagggca ccgagatgaa caccacgggg ctatgtgcct gtccagggtc    4080
atcctaggct taaggccacg acactcaagg acgtggtggg cggcgtcgcg gaggtgctcc    4140
aagcgaacaa gctggccacc aaggaggacg ccgacaaggt ggcggccacc gctatgcaga    4200
acgatgggag gcacgccggt gacgacaagg agctaacacg atccatttag tcccgatccg    4260
agttgatcag gaattcaatc ctgcaccttg cggttacgtt tttcttctcc gcgggaaaag    4320
caatcaccga tggtagggac aaagtgtgtg tgagaacgga ggccaggcca agtgcgtgc    4380 gagaacggag gctaggccat cgctggattg gatttacgaa tgaaatatng atgtgacgaa    4440
cagaaaatta tcagtttgat ttaattttca taatcggagc tctttaatag gaaaaaaaat   4500
tacatgtacg ttccttcatn gtgcccatgt ccatccggga gtccaggttt attcncaaag    4560
ncncaatcaa cagctannaa tccatgtcct tccccgccgt tccctactct gctttttttt    4620
ctttcatttg aaaccttccg ctatgaattt ctagtcgttc ctagcatcca cgcacacaaa    4680
atagatttcc ctcgcaaggc aaaacataca aatatgagtg catgcaagat attacaaacc    4740
caatccatta aaaatagaac ataattaact ttagcctacc tatctcaata ttggtatatg    4800
```

```
cccaaactca aaaggagaaa aancaaacta aaacttttaa taaagtgacc ccaagagata    4860
aaaaggtgat agtaacaaca aaatctcact tgacaatgtc gttgatcagc actattttta    4920
aatattactt aaaaatcttt atatttacct attaaaacaa tgaaaaacag aagatgtttc    4980
ttttttattt acaacagcgt tgtatttagt catgtcctat ctaagagaga aaaatgaatt    5040
taacgaaaag aagctcagaa aaaaaaaaga gaacagggcc accacaccag taatccctat    5100
gttatcaatg aaaaaaaatt tcaatgctag gttttttata agaaaggtg ataaagtgtt     5160 gaaaatacag caggaaattt atatatcttg ctggtttaac attaattcaa gcatatagat    5220
ataaaaatat atcaggctag gaaaggaaaa ggataaaatt ggagagaaaa aggaaaagaa    5280
cagtagagga taaccagcaa aaagatgaaa ggattcgaac ccatgaccta gcgttacaat    5340
tgtttcacag gctaaccaat cgagaatcat cgacgtagtg taatcttgtg tagctacatt    5400
tgaaaaaata tgttttgagc tgaacgttgg tgtgtccgcc cctgcatccg atacatgttg    5460
gagcgtggag cgcggtaata tctccttctc tctcgtcgct ttctgcgtct ccccgtctct    5520
ccttcgccaa cagccgagaa gaggcagaga gagcgccgcc ccccgtccct ctctctccct    5580
ctcgtcctcg cccccatccc tctcgtcttt cccttgccgg cagcagagga ggcggcagcg    5640
acggcttcag ctgctcccac gggccggatc gggcagtggc ggtggcgtcg gcggcttccg    5700
ctggcgaatc cggcgggtga atcgggtgaa atttgggtga ccccgatac aaatcagtgt     5760 tccgataggt aataccctgc tctcagcatc tgcccttttg aattcgccaa gagccagcat    5820 ctgcccttttt gaattcgcca agggccagca tctgcccatt tgattttgaa ttcgccaaga    5880
gccagcaaca gcgccccgc gccccctccc tcctccgcaa taaacagcca cacgcgccgc     5940
ccccatgtcc accctcatcg ccacagcgca ccaccaccac caccaccacc accaccaccg    6000
tctccagcca tggcctcctc cgcctccctg cagcgcttcc tccccccgta cccccacgcg    6060
gcagcatccc gctgccgccc tcccggcgtc cgcgcccgcc ccgtgcagtc gtcgacggtg    6120
tccgcaccgt cctcctcgac tccggcggcg gacgaggccg tgtcggcgga gcggctggag    6180 ccgcggggtgg agcagcggga gggcggtac tgggtgctca aggagaagta ccggacgggg      6240
ctgaacccgc aggagaaggt gaagctgggg aaggagccca tgtcattgtt catggagggc    6300
ggcatcaagg agctcgccaa gatgcccatg gaggagatcg aggccgacaa gctctccaag    6360
gaggacatcg acgtgcggct caagtggctc ggcctcttcc accgccgcaa gcatcagtgt    6420
atgcctctct tctcttgctc ctctgatcaa cacattttct tgctttcgtt cggttatttg    6480
tcgcgccgag gaagttaatt cgccaagata ttctgcagtt ttttttctcg atgcacattc    6540
agcaacctaa ttaagactga ttaagttgct gtgattttta tagcttaatt acggtctcgt    6600
gggtaatgac tatttatatt gagtaaacat ggttacctttt gatccaatca cttcacctcc    6660
atgtgccata tatagccaca ggctctacca agtaacacta gtaatatgcc cgtgctacga    6720
cacggtggca aataaatca ttaaattta ttataatcaa attaaggatc ctaaaattgg        6780
tccaattggg tgttaattcg atgcaggtca tataaaaata tattttaggc aaggtgcaat    6840
tcaagagcat caaccattat atccaatcac tttaatatat atttgaagat aacatatgtc    6900
ggaaaaaaaa tgatggagag ctatttcatt aacttgtgag cataaacaga tcaccagatg    6960
atgccaccat aagtcccgcc acagtaagtg atgcagctca tcttgcccta ggcgttcggt    7020
ctaaccagta gatagaaaga gtacaacata gatcgaatga aaaaaaaaat ctccagaaga    7080
aagctcaacc acattgagta aattagagca acaatcaaat cgagtcagca tatcgttatg    7140
ttagcagaac caatcaccac aatttgtttc tcctctttat ctaagngttt tggccaggtt    7200
```

```
aaaagcatat atcactatgt tccaagcaaa catcggcaat ggacacgtca aaaataaatg      7260
atcaattgtt tctttgagta caaaattgac aatggacact atgttccttt gttagaattc      7320
tatttgtcag ggtaggatgt agaaaaactt aacttttaga ggaagcttaa atatccggca      7380
taaacttgct ttttcagcgc tctataaaat aattcaacag tgaattgtcc atcttttcta      7440
agtgctccaa aagacactaa gttgaaaaac caggtgaacc aacagattga tccacaaaat      7500
cttattatta gattattcac ttaaaagcct gtctttattt caaacatata aaacagaag      7560 ttattaatca gggaagcgct tatggcagcc tgagcgaacc agtgatagca agtggtgaaa      7620
acagtaaata ggatacataa aaattataca aggtttctac tgtttatcga aaaaaaatat      7680
ttgaaaacag taaataggat acataatcga cttccaactt gtccttatca taacatccag      7740
aatcacaaca agaattgcaa cgaatacata gtcgacttga gctaagaagt cacaagacct      7800
gtcaaagtaa gctgcccttg atcttgaagt gaaaggcata ttttattgtc ttccttggca      7860
aacagatatc actgtcttca gcagttcagt tagataatcc aagatttctc acggagaaga      7920
gcatatcact cacatcagtg ttgtgccctc caaatactga gataaactga attttgttct      7980
ctttgaagca tctgcaggca ttaacaataa taatacttta caaagtttca ttgggtctaa      8040
actattgttt gcacatcata tatatgccca gaacttttta gcatgataca agggtcctgt      8100
tcataactca tgcctaaatc tgacaaattt gtcaaacgac aatataagtc gaattataat      8160
gcgttttaga attgacgcca aaacttttgc tagcgtaagt aactcttcca cctcccagca      8220
tgcatacaac caacaagcta aacttttgtt caaaaaaatg tacatttatt tccttgaaca      8280
cagcctttgt agaatatgat taaaaactca tggatgaatg aaataatgta aaagaatggt      8340
caaaatgatg aatagtacaa gaagcaactg tgaacatttc acctttacct gactgttcgc      8400
aagaaggcca cgtggcagaa aagccagaaa tgcaagaagc ttccctaatt gatacaccat      8460
caagaaatca atggactcaa caccagcgtc cgcccagaca aaatgaatgc aggcacctaa      8520
aatatagaac cattgacttt tcaacactga attatataac ctgaatatct tgttttgtta      8580
acacatctga caaaatcagt gcattctgtt ccatatagat gtatgcatag ctcccatatg      8640
ttagttgatc gatgagcatg caaactatac acaccttacg ttactccctc tgtcaaaaaa      8700
aatataagct tgtctagata catagctaca aatgcttata ttttggatt ctcttaaagc      8760 tgtagaaact tttatcgccc cgccatggca agtcgagctg ccatccccaa tgaaagcccc      8820
cacacaggtt tcatgccctg ctgcacaata ttgagcaacc aaaaatataa taatatttgt      8880
gtcagaattt gaatcaacct tacagatact gggtggccag aaaatctagt ccaagtaata      8940
tcctgaaaaa tagcaactgg caaatactaa aggcagtgaa gagtttcctt tagatcagat      9000
gataaaaaaa aatcatatgt tcaatagcaa taatcactca catttttttt gctgtttaga      9060
atttagataa atagtagtta aacttctata gcttgcgtag ctaagatcaa tggtgattat      9120
tagttgaaaa aataatcaaa tcatcaaact gaggagactt ataccctgcca taagttctga      9180 aatttcaatg atcctagtca atatttactg tatatataga attaggtcca aaagatgata      9240
cttacaatta aggatgttgt attgatcggt tcataactca agcttctatt tatcattaat      9300
caaaagctgg atcattcatg catataacctt tgccgcactc aacatagcag ctcggagtct      9360
tctttgttca gaagcgagga aggagtcaac aaataagtac tgcaatgtta aacaaaccga      9420
catatcaaat cccaaattaa gaatgcatga tttattaata caggaaatat atgatcaagt      9480
cccaaaaagt gagtcatgtt atgtacactc agtcatcaat ttcaataaga atattaactt      9540
gctcattggt atatggattt gattatgaca taatttgaca atacatttac agaataaact      9600
```

```
tgcagtgctg tgagcatatg ttactaacat gtaaggacct tgttttgctc tgttcaatac    9660
tcatgttgat cttgatctgt gtccacatat acctaaatga aatgaaatca agaatgagg     9720 tttgtaggag tggagttggt gaattatagg gtagataatg tcggcacaac cgtttgataa    9780
gtagtacgag tactttattt ggcgccaccg cgccagcatc agatgtgtgg cctttgcact    9840
gattgaaccc aaaagaaaaa aaaagtcgt tttggtccca cacaattcta cttcatctgc     9900
aggatgtaca gaaggttaca tatctattct gttctatgct ctgtttacat ttataagggc    9960
tcacttggtg gctgtcattg gttggctggt gcggtatatt actaataggt tttttaatgg   10020
catatatgtt cttaaaataa accagaaaag caaaagatca actatcttag ccacaccaat   10080
gaaatggaat atactgaact gtcacggcta aaattctctt cagtcacctg cccagctgg    10140 agccgtgggc tcgtcgtctt ttctaaacat gtactagtat tttgggggcc cacagtgaat   10200
ttggcccaaa atgctgacag ccgctctacg gctctacgct gtgcagatgg gcggttcatg   10260
atgcggctga agctgccaaa cggtgtgacg acgagcgagc agacgaggta cctggcgagc   10320
gtgatcgagg cgtacggcaa ggagggctgc gccgacgtga caacccgcca gaactggcag   10380
atccgcggcg tcacgctccc cgacgtgccg gccatcctcg acgggctcaa cgccgtcggc   10440
ctcaccagcc tccagagcgg catggacaac gtccgcaacc ccgtcggcaa cccgctcgcc   10500
ggcatcgacc ccgacgagat cgtcgacacg cgatcctaca ccaacctcct ctcctcctac   10560
atcaccagca acttccaggg caaccccacc atcaccaacc tgtgagtgat cgaatcaact   10620
tgatcatgct ctgtgctgtg ctgttcgtgt cgtctctgac gacatgtttg ttgaatttgt   10680
tgttgctgcg tgctgttggc aggccgagga agtggaacgt gtgcgtgatc gggtcgcacg   10740
atctgtacga gcacccgcac atcaacgacc tcgcgtacat gccggcggtg aagggcggca   10800
agttcgggtt caacctcctt gtcggcgggt tcatcagccc caagaggtgg gaggaggcgc   10860
tgccgctgga cgcctgggtc cccggcgacg acatcatccc ggtgtgcaag gccgttctcg   10920
aggcgtaccg cgacctcggc accaggggca accgccagaa cccgcatg atgtggctca    10980 tcgacgaact tgtgagcctc cattcatcca cgccattgac tgaattacgt atgtcccaat   11040
gttcttatca gttaattgcg gtgttggcat tgcagggaat ggaggctttt cggtcggagg   11100
tggagaagag gatgccgaac ggcgtgctgg agcgcgctgc gccggacgac ctcatcgaca   11160
agaaatggca gaggagggac tacctcgcg tgcacccgca gaagcaggaa gggatgtcct   11220
acgtcggcct gcacgtgccc gtcggccggg tgcaggcggc ggacatgttc gagctcgccc   11280
gccttgccga cgagtatggc tccggcgagc tccgcctcac cgtggagcag aacatcgtga   11340
tcccgaacgt caagaacgag aaggtggagg cgctgctcgc cgagccgctg cttcagaagt   11400
tctccccgca gccgtcgctg ctgctcaagg gcctggtcgc gtgcaccggc aaccagttct   11460
gcggccaggc catcatcgag acgaagcagc gggcgctgct ggtgacgtcg caggtggaga   11520
agctcgtgtc ggtgccccgg gcggtgcgga tgcactggac cggctgcccc aacagctgcg   11580
gccaggtgca ggtcgccgac atcggcttca tgggctgcct caccaaggat agcgccggca   11640
agatcgtcga ggcggccgac atcttcgtcg gcggccgcgt cggcagcgac tcgcacctcg   11700
ccggcgcgta caagaagtcc gtgccgtgcg acagctggcc gccgatcgtc gccgacatcc   11760
tggtcgagcg gttcggggcc gtgcggaggg agagggagga ggacgaggag taggagcaca   11820
gactggggtg gtttgcttgc tccggtgatc tctcgccgtc cttgtaaagt agacgacaat   11880
atgccttcgc ccatgcacg cttgtactgt cacgttttgg tttgatcttg tagcccaaaa    11940
gttgtgttca ttctcgttac agtcttacag aggatgattg attgataaat aaanaagaaa   12000
```

-continued

| | |
|---|---|
| cagattctgc aactgttcat cgctgttcct aaatctgatt tcgcgatagt atcttgtctg | 12060 |
| acctgtccca atcgcagtgc taaaaccata taatcttgca agcaaatgaa attgaaagag | 12120 |
| ttcaatgcaa ccactaacgg tctaacaaca tgataaggcc t | 12161 |

<210> SEQ ID NO 2
<211> LENGTH: 12179
<212> TYPE: DNA
<213> ORGANISM: Oryza sativa

<400> SEQUENCE: 2

| | |
|---|---|
| ctcgagcttt tttgactgcc ctaatcaggc gggttccttg tgggacccac ataatgcttt | 60 |
| ttttaatcgc cttcacgggc tgcatgcaaa ctatacggcg tggtacttcc actactagaa | 120 |
| aaaacgggct tttcgcaggc gggcaaacct tccgcatgta tattaacgac cgtaaaaatc | 180 |
| tccaattttc acaggtggac cccagcaccg cctgcgaaaa taattttcgc aggctgcatt | 240 |
| tcgaatcttc ctgggtgcta cagtaaacca cctgcgaaaa tactcacggc gccaaaaaaa | 300 |
| aaatttccgc cagccccgcc ccctccctat tcaaatcaca aattctcaca aatctcatcc | 360 |
| aaaaacaaaa ttcaatccaa aaatccatac atcaacacaa agcattggat tcaaatccac | 420 |
| aacatcaatt tacaagttaa catcaatcaa catgtaagct ttaaaacgaa acgtcgtcgt | 480 |
| cgccggcaaa ctccttttgc atgcggtgcc gccgccgccc ccctccccccc tctgtccgga | 540 |
| tttgggaggg agggaggtgt ttgccgccac caccgccctc ccctctcctc gtagggccgg | 600 |
| atctcgggag ggaggagagg ggagccgcct ccgcacagcc atcaacgtcc gtgccgccgt | 660 |
| cgcctcgttc gcaccaccgc cgttgcttcc cctcctccgg ccagatctag agcggggag | 720 |
| gaagagaggg ggagccaccg ccaccgtcgc cccctcgcgt ccgcgccgtc gtcaccgtcc | 780 |
| acgccgccgc gtccgtgccg ccgctgtcgc tcccctcct ctggcgagga gggagagaga | 840 |
| gggagccgtc gcgccgccgt cgctccccctc cttcggcgag gagggagaga ggggaggga | 900 |
| agagggatgg aggggaggag agtggcgctg agagagagag agagagacgc tgaggagagg | 960 |
| aaatgagtgg tggggagggg tggaggagaa gataaggagg acttagatt tttttttggg | 1020 |
| taagtatgat ttttgcaggc ggaccacata aggttccgcc tgcgaaaatc aatttttcg | 1080 |
| cgcagaccac ttaagaggtc cgcatgcgaa aataaaggta ttttttaggg cggacctctt | 1140 |
| aagtggtccg cctggaaaaa ttgattttcg caagcggatg acgaaaattc accccggttt | 1200 |
| atatttcga agatgcttca tcgacgacat cgactgcgtc ctctatgaca gcaacgaccg | 1260 |
| cgtcaccgac gacggcatcg atcacgtcat ctacgatgac aatgactgca tcaactccgc | 1320 |
| atcactattg tgatgactgt tacacggcgt agaagaacca accaaagtgg tggcttcatc | 1380 |
| gccaacgacg tcctctaaca tatgcaagac gtccccaatg gcatcctctg acatctacaa | 1440 |
| ggtgcaagat gctaacaatt acagttttg tcttcacact gtggcataaa tatttttt | 1500 |
| caccttcggc tatatgcggc tacacctaca accacggtta ctacatgatc ggctccatca | 1560 |
| acgaacatct ataacaacaa tcattgatgg aaactctagt caaagcgtct gtgtcatcgc | 1620 |
| tatcatccat gacactcccg ctatgactac gtgagggaat agataagagt caagggacga | 1680 |
| cacggaagga gacgtaggca ccaggtggag gaccatccat caaagatgca attgatgatg | 1740 |
| gtgagttgaa gaagatgaag aaataaaata tttcaaatcc agtcgcaatc attcgcttcg | 1800 |
| ctcccgttac gactgagggg gaatgttaga agcatagata tattaattgg agataagagt | 1860 |
| catacaaata tagagataag atatcatcct agagatagaa tcctagagat aaaatatagt | 1920 |
| cctagagata aatctactct tacttgtacc cctatatata ccccatgaga ggatcaatgc | 1980 |

```
aatacaccga gaatacaaca attagatttt tctacggttg taactataat acgctgtaat    2040
atgctggatc ggggaagagc gcccgtaatc agtgccccag agatgtaggt ctcggttgaa    2100
ctccattatc aaataccgta cctcggtgtc gtcatcatgt ttgaatcttc tatgacgttt    2160
cttttgcatt cggttttcga tgtgacttcg gggctggttt tataacaatg attatagtgc    2220
tgttgacggc aatcggttgt gagaattagc tattcgggtc cctccatgtg attttcttgt    2280
gattgggatg tatggtaatg ctagggtttt aaggtgtagg attggtgcat gagagatcat    2340
cacttcactt gtatgacctt ctctccttt atattttttt atcattctct ccttttttt     2400 ataatgctac tgaactagtg gaatacaggg gactaatgca aaataaaaga aaagtatcac    2460
tggtcacggc atataattta gaaagtgtgt gatttaggca tagggctgac catgacccett   2520 tacgacttgg tcgctcggtt tgttagacga tagatcaacc aacaaaagct acgatacatg    2580
atgtacgtgt caggatacaa atccttacaa ataacaacag ttattgttcg ataactatca    2640
gttgtctagg cttaccaatg tataatagaa gatgaaaatt ccatattact ggtatcgttc    2700
aatgctagta actctttgag ctttgtctag gttaaaaaaa aaattatgga tccaccatca    2760
caaaaatgaa aaacaccggg gaaaacaaaa aaccatttga tagcagcaca agacaaaatg    2820
atgttaccgt ctacccgagc tcctactccg taccagcaca accaaacgaa cagtacccgc    2880
cggaccaggg gcacgttcgt aaatttccct cccgtggctg gctggctgcc atctctctca    2940 accaggggttg gtaatttcgg ccgtttcggt gggtcccgat agtaaatgag ctccggtcaa   3000
aacgccctcc gcctccctc attgcgccgc acgcacaccg catctagatc cagatcgaaa    3060
aaatcgctat ctcgccgagt cgccagtcac cgcctcgacg ccggtcgccg taccgccggc    3120
gctgcacgcc cccctccaag ccgtcgcccc atcgcccca gccgccagt ggtggggcgg     3180 cggatgccga gcttggcgag gttgccgagg acgaaccagg cgaggaggac gaggatcttg    3240
tcgacgagcc agagcgggag ccacgccatg agcaacacgg cgagctcgaa cgtggacttg    3300
ccgagcacct cgccagggag gacgtggacg gcgtcgcgca ccaccatcgc cgggagggcg    3360
ctgtggtcgc acaggtcgag cgacaccacc atgccggagt tgccgcaccc gacgacgagc    3420
accttcttgc cgcggtacgc ctcgccggac ttgtagaccg cgacatgcat cacctcgctg    3480
ctatatttgt tcttggactg tggagacttg ctgtcagtgg gtgtgttcag aattgctgct    3540
gcagcttgca gcgaatttgt gatgcagcag ctgcagcttg tatggctgcc gagtagagcg    3600
agtgttgcta tctgttttttg ttctcttttt cagaaatttc gcccgcaaat tttaaatttg    3660
aattcaaatt tttaaaagaa ctagaaaata tgcccgtgcg ttgcaccggg tgaatatcaa    3720
acaaatattg atgggtaaga ttgcttgtgt acttataaca catatgcaca aaaatattga    3780
atatgtacat acctcgcaaa tatctccaaa ttttatacat atgagttgtg taaatcatgt    3840
gagttccata ttgtcatgtt aatatggagt attactgatg agcccatcta tggtgataat    3900
tttggaggtt gtagctcaac gaatttgtat ttgctatgta tctcaacgtt gataagtcac    3960
tactacaacc atcggcgacc tttctcggga tccaagcatg tcgacccgc caacgtggcg     4020 tcggtgcagg gcaccgagat gaacaccacg gggctatttg cctgtccagg gtcatcctag    4080
gcttaaggcc acgacactca aggacgtggt aggcggcgtc acagaggtgc tcccagcgaa    4140
caagctggcc accaaggagg acgccgacaa ggtggcggcc accgctatgc agaaacgatg    4200
ggaggcatgc cggtgacgac aaggagctaa cacgatccat ttagtcccga tccgagttta    4260
tcaggaattc aatcctgcac cgtgcggtta cgttttctt ttccgcggga aaagcaatca     4320
ccgatggtag ggacaaagtg cgtgtgagaa cagaggccag gccaaagtgc gtgcgagaac    4380
```

```
ggaggctagg ccatcgctgg attggattta cgaatgaaat atcgatgtga cgaacagaaa    4440
attatcagtt tgatttaatt ttcataatca gaactcttta ataggaaaaa aattacatgt    4500
acgttccttc atcgtgccca tgtccatctg ggagtccagg tttattcaca aagacccaat    4560
caacagccag gaatccatgt ccttccccgc cgttccctac tctgctttt tttctttcat    4620 ttgaaacctt ccgctatgaa tttctagtcg ttcctagcat ccacgcacac aaaatagatt    4680
tccctcgcaa ggcaaaacat acaaatatga gtgcatgcaa gatattacaa acccaatcca    4740
ttaaaaatag aaaataatta actttagcct acctatctca atattggtat atgcccaaac    4800
tcaaaaggag aaaaaccaaa ctaaaacttt taataaagtg aacccaagag ataaaaaggt    4860
gatagtaaca acaaaatctc acttgacaat gtcgttaatc aacactgttt ttaaatatta    4920
cttaaaaatc tttatttta cctattaaaa caatgaaaaa cagaagatgt ttcttttta    4980 tttacaacag cgttgtattt agtcatgtcc tatctaagag agaaaaatga atttaacgaa    5040
aagaagctca gaaaaaaaaa gagaacaggg ccaccacacc agtaatccct atgttatcaa    5100
tgaaaaaaaa tttcaatgct aggttttta taagaaaagg tgataaagtg ttgaaaaaat    5160
acagcaggaa attatatatc ttgctggttt aacatgaatt caagcatata gatataaaaa    5220
tatatcaggc taggaaagga aaaggataaa attggagaga aaaggaaaa gaacagtaga    5280 ggataaccag caaaaagatg aaaggattcg aacccatgac ctagcggtac aattgtttca    5340
caggctaacc aattgagaat catcgacgtt gtgtcatctt gtgtagctac atttgaaaaa    5400
atatgttttg agctgaacgt tggtgtgtcc gccctgcat ccgatacatg ttggagcgtg    5460
gagcgcggta aagaaaaaat cctatcgaac cttatctcct tctctctcgt cgctttctgc    5520
gtctccccgt ctctccttcg ccaacagccg agaagaggca gagagagcgc cgccccccgt    5580
ccctctctct ccctctcgtc ctcgccccca tccctctcgt cttttccctg ccggcagcag    5640
aggaggcggc agcgacggct tcagctgctc ccacgggccg gatcgggcag tggcggtggc    5700
gtcggcggct tccgctggcg aatccggcgg gtggatacaa atcagtgttc cgataggtaa    5760
aaccctgctc tcagcatctg ccctttgaa ttcgccaaga gccagcatct gcccttttga    5820
attcgccaag ggccagcatc tgcccatttg attttgaatt cgccaagagc cagcaacagc    5880
gcccccgcgc ccctcccctc ctccgcaata acagccaca cgcgccgccc ccatgtccac    5940
cctcatcgcc acagcgcacc accaccacca ccaccaccac caccaccacc gtctccagcc    6000
atggcctcct ccgcctccct gcagcgcttc ctccccccgt accccacgc ggcagcatcc    6060 cgctgccgcc ctcccggcgt ccgcgcccgc cccgtgcagt cgtcgacggt gtccgcaccg    6120
tcctcctcga ctccggcggc ggacgaggcc gtgtcggcgg agcggctgga gccgcgggtg    6180
gagcagcggg agggccggta ctgggtgctc aaggagaagt accggacggg gctgaacccg    6240
caggagaagg tgaagctggg gaaggagccc atgtcattgt tcatggaggg cggcatcaag    6300
gagctcgcca agatgcccat ggaggagatc gaggccgaca gctctccaa ggaggacatc    6360 gacgtgcggc tcaagtggct cggcctcttc caccgccgca agcatcagtg tatgcctctc    6420
ttctcttgct cctctgatca acacatttc ttgctttcgt tcggttattt gtcgcgccga    6480
ggaagttaat tcgccaagat attctgcagt ttttttctc gatgcacatt cagcaaccta    6540
attaagactg attaagttgc tgtgatttt atagcttaat tacggtctcg tgggtaatga    6600
ctatttatat tgagtaaaca tggttacctt tgatccaatc acttcacctc catgtgccat    6660
atatagccac aggctctacc aagtaacact agtaatatgc ctgtgatacg ccacggtggc    6720
ataataaatc attaaatttt attataatca aattaaggat cctaaaattg gtccaattgg    6780
```

```
gtgttaattc gatgcaggtc atataaaaat atattttagg caaggtgcaa ttcaagagca      6840
tcaaccatta tatccaatca ctttaatata tatttgaaga taacatatgt cggaaaaaaa      6900
atgatggaga gctatttcat taacttgtga gcataaacag atcaccagat gatgccacca      6960
taagtcccgc cacagtaagt gatgcagctc atcttgccct aggcgttcgg tctaaccagt      7020
agatagaaag agtacaacat agatcgaatg aaaaaaaaaa tctccagaag aaagctcaac      7080
cacattgagt aaattagagc aacaatcaaa tcgagtcagc atatcgttat gttagcagaa      7140
ccaatcacca caatttgttt ctcctcttta tctaagtgtt ttgccaggtt aaaagcatat      7200
atcactatgt tccaagcaaa catcggcaat ggacatgtca aaaataaatg atcaattgtt      7260
tctttgagta caaaattgac aatggacact atgttccttt gttagaattc tatttgtcag      7320
ggtaggatgt agaaaaactt aacttttaga ggaagcttaa atatccggca taaacttgct      7380
ttttcagcgc tctataaaat aattcaacag tgaattgtcc atcttttcta agtgctccaa      7440 aagcactaa gttgaaaaac caggtgaacc aacagattga tccacaaaat cttattatta      7500
gattattcac ttaaaagcct gtctttattt caaacatata aaaacagaag ttattaatca      7560
gggaagcgct tatggcagcc tgagcgaacc agtgatagca agtggtgaaa acagtaaata      7620
ggatacataa aaattataca aggtttctac tgtttatcaa aaaaaaatat ttgaaaacag      7680
taaataggat acataatcga cttccaactt gtccttatca taacatccag aatcacaaca      7740
agaattgcaa cgaatacata gtcgacttga gctaagaagt cacaagacct gtcaaagtaa      7800
gctgcccttg atcttgaagt gaaaggcata ttttattgtc ttccttggca aacagatatc      7860
actgtcttca gcagttcagt tagataatcc aagatttctc acggagaaga gcatatcact      7920
cgcatcagtg ttgtgccctc caaatactga gataaactga attttgttct ctttgaagca      7980
tctgcaggca ttaacaatta taatacttta caaagtttca ttgggtctaa actattgttt      8040
gcacatcata tatatgccca gaacttttta gcatgataca agggtcctgt tcataactca      8100
tgcctaaatc tgacaaattt gtcaaacgac aatataagtc gaattataat gcgttttaga      8160
attgacgcca aaacttttgc tagcgtaagt aactcttcca cctcccagca tgcatacaac      8220
caacaagcta aactttgtt caaaaaatg tacatttatt ccttgaaca cagcctttgt      8280 agaatatgat taaaaactca tggatgaatg aaataatgta aaagaatggt caaaatgatg      8340
aatagtacaa gaagcaactg tgaacatttc acctttacct gactgttcgc aagaaggcca      8400
cgtggcagaa aagccagaaa tgcaagaagc ttccctaatt gatacaccat caagaaatca      8460
atggactcaa caccagcgtc tgcccagaca aaatgaatgc aggcacctaa aatatagaac      8520
cattgacttt tcaacactga attatataac ctgaatatct tgttttttta acacatctga      8580
caaaatcagt gcattctgtt ccatatagat gtatgcatag ctcccatatg ttagttgatc      8640
gatgagcatg caaactatac acaccttacg ttactccctc tgtcaaaaaa aatataagct      8700
tgtctagata catagctaca aatgcttata ttttggatt ctcttaaagc tgtagaaact      8760
tttatcgccc cgccatggca agtcgagatg ccatccccaa tgaaagcccc cacacaggtt      8820
tcatgccctg ctgcacaata ttgagcaacc aaaaatataa taatatttgt gtcagaattt      8880
gaatcaacct tacagatact gggtggccag aaaatctagt ccaagtaata tcctgaaaaa      8940
tagcaactgg caaatactaa aggcagtgaa gagtttcctt tagatcagat gataaaaaaa      9000
aatcatatgt tcaatagcaa taatcactca catttttttt gctgtttaga atttagataa      9060
ttagtagtta aacttctata gcttgcgtag ctaagatcaa tggtgattat tagttgaaaa      9120
aataatcaaa tcatcaaact gaggagactt atacctgcca taagttctga aatttcaatg      9180
```

```
atcctagtca atatttactg tatatataga attaggtcca aaagatgata cttacaatta      9240
aggatgttgt attgatcggt tcataactca agcttctatt tatcattaat caaaagctgg      9300
atcattcatg catataccct tgccgcactc aacgtagcag ctcggagtct tctttgttca      9360
gaagcgagga aggagtcaac aaataagtac tgcaatgtta aacaaaccga catatcaaat      9420
cccaaattaa gaatgcatga tttattaata caggaaatat atgatcaagt cccaaaaagt      9480
gagtcatgtt atgtacactc agtcatcaat ttcaataaga atattaactt gctcattggt      9540
atatggattt gattatgaca taatttgaca atacatttac agaataaact tgcagtgctg      9600
tgagcatatg ttactaacat gtaaggacct tgttttgctc tgttcaatac tcatgttgat      9660
cttgatctgt gtccacatat acctaaatga aatgaaatca agaatgagg tttgtaggag       9720
tggagttggt gaattatagg gtagataatg tcggcacaac cgtttgataa gtagtacgag      9780
tactttattt ggcgccaccg cgccagcatc agatgtgtgg cctttgcact gattgaatcc      9840
aaaagaaaaa aaagtcgtt ttggtcccac acaattctac ttcatctgca ggatgtacag       9900
aaggttacat atccattctg ttctatgctc tgtttacatt tatatttata gtactaggtt      9960
gaaagggctc acttggtggc tgtcattggt tggctggtgc ggtatattac taataggttt      10020
tttaatggca tatatgttct taaaataaac cagaaaagca aaagatcaac tatccttagcc     10080
acaccaatga aatggaatat actgaactgt cacggctaaa attctcttca gtcacctggc      10140
ccaactggag ccgtgggctc gtcgtctttt ctaaacatgt actagtattt tggggggccca     10200
cagtgaattt ggcccaaaat gctgacagcc gctctacggc tctacgctgt gcagatgggc      10260
ggttcatgat gcggctgaag ctgccaaacg gtgtgacgac gagcgagcag acgaggtacc      10320
tggcgagcgt gatcgaggcg tacggcaagg agggctgcgc cgacgtgaca acccgccaga      10380
actggcagat ccgcggcgtc acgctccccg acgtgccggc catcctcgac gggctcaacg      10440
ccgtcggcct caccagcctc cagagcggca tggacaacgt ccgcaacccc gtcggcaacc      10500
cgctcgccgg catcgacccc gacgagatcg tcgacacgcg atcctacacc aacctcctct      10560
cctcctacat caccagcaac ttccagggca accccaccat caccaacctg tgagtgatcg      10620
aatcaaattg atcatgctct gtgctgtgct gtttcgtgtc gtctctgacg acatgtttgt      10680
tgaatttgtt gttgctgcgt gctgttggca ggccgaggaa gtggaacgtg tgcgtgatcg      10740
ggtcgcacga tctgtacgag cacccacaca tcaacgacct cgcgtacatg ccggcggtga      10800
agggcggcaa gttcgggttc aacctcctcg tcggcgggtt cataagcccc aagaggtggg      10860
aggaggcgct gccgctcgac gcctgggtcc ccggcgacga catcatcccg gtgtgcaagg      10920
ccgttctcga ggcgtaccgc gacctcggca ccaggggcaa ccgccagaag acccgcatga      10980
tgtggctcat cgacgaactt gtgaaccatt tttttctcca ttcatccacg ccattgactg      11040
aattacgtat gtcccaatgt tcttatcagt taattgcggt gttggcattg cagggaatgg      11100
aggcttttcg gtcggaggtg gagaagagga tgccgaacgg cgtgctggag cgcgcggcgc      11160
cggaggacct catcgacaag aaatggcaga ggagggacta cctcggcgtg cacccgcaga      11220
agcaggaagg gatgtcctac gtcggcctgc acgtgcccgt cggccgggtg caggcggcgg      11280
acatgttcga gctcgcacgc ctcgccgacg agtacggctc cggcgagctc cgcctcaccg      11340
tggagcagaa catcgtgatc ccgaacgtca agaacgagaa ggtggaggcg ctgctctccg      11400
agccgctgct tcagaagttc tccccgcagc cgtcgctgct gctcaagggc ctcgtcgcgt      11460
gcaccggcaa ccagttctgc ggccaggcca tcatcgagac gaagcagcgg gcgctgctgg      11520
tgacgtcgca ggtggagaag ctcgtgtcgg tgccccgggc ggtgcggatg cactggaccg      11580
```

-continued

```
gctgccccaa cagctgcggc caggtgcagg tcgccgacat cggcttcatg ggctgcctca    11640
ccaaggacag cgccggcaag atcgttgagg cggccgacat cttcgtcggc ggccgcgtcg    11700
gcagcgactc gcacctcgcc ggcgcgtaca agaagtccgt gccgtgcgac gagctggcgc    11760
cgatcgtcgc cgacatcctg gtcgagcggt tcggggccgt gcggagggag agggaggagg    11820
acgaggagta ggaacacaga ctggggtgtt ttgcttgctc cggtgatctc tcgccgtcct    11880
tgtaaagtag acgacaatat gccttcgccc atggcacgct tgtactgtca cgttttggtt    11940
tgatcttgta gcccaaaagt tgtgttcatt ctcgttacag tcttacagag gatgattgat    12000
tgataaataa agaagaaaca gattctgcaa ctgttcatcg ctgttcctaa atctgattta    12060
gcgaaagtat cttgcctgac ctgtcccaat cgcagtgcta aaaccatata atcttgcaag    12120
caaatgaaat tgaaagagtt caatgcaacc actaacagtc taacaacatg ataaggcct     12179
```

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
gtaggtgcaa agtgtgcc                                                       18

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
cagcatggtg taccagga                                                       18

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ctctttaggg tgttaccatg                                                     20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ggaattcaga gacaacatgg                                                     20

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
gcttcagtgt tgtgtgattc tg                                                  22

```
<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttcttcctcc agtaccagat                                                  20

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
cctaatgggc cgaatttata acg                                              23

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
gcgaaaggcg aggttgatg                                                   19

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
caaagtaatt tgggatcttt ac                                               22

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
tccctgctgc taggatcttg                                                  20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
atccatcaag tcagcaggtg                                                  20

<210> SEQ ID NO 14
<211> LENGTH: 18
<212> TYPE: DNA
<213> ORGANISM: Artificial
<220> FEATURE:
<223> OTHER INFORMATION: primer
```

<400> SEQUENCE: 14
gctgtgaatg gatgccaa 18

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
cttgtaacag gtgtcctcga 20

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
caataacagc ctgcaacgaa c 21

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
ggctgaccaa caaaagaca 19

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gaaacgggat gtcaacacag 20

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
gacagcttga acaattgact gg 22

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
cacaactcac aagtaacaaa c 21

<210> SEQ ID NO 21
<211> LENGTH: 20
<212> TYPE: DNA

```
<213> ORGANISM: Artificial
<220> FEATURE:
<223> OTHER INFORMATION: primer

<400> SEQUENCE: 21
gattcgaacc catgacctag                                                 20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gacacaccaa cgttcagctc                                                 20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
ttcgaaccca tgacctagcg                                                 20

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
ctgaggatga acctacaatg g                                               21

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
cgtgctgcta attactcatg c                                               21

<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
agtaatggat ccaggaacat g                                               21

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
ccgtgttttt cgattggcac                                                 20
```

```
<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
gatgattagc tgtcctgtcc                                                 20

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
ctttcttgtt ggttgtagta gcta                                            24

<210> SEQ ID NO 30
<211> LENGTH: 17
<212> TYPE: DNA
<213> ORGANISM: Artificial
<220> FEATURE:
<223> OTHER INFORMATION: primer

<400> SEQUENCE: 30
gaggccattc tcgcaac                                                    17

<210> SEQ ID NO 31
<211> LENGTH: 19
<212> TYPE: DNA
<213> ORGANISM: Artificial
<220> FEATURE:
<223> OTHER INFORMATION: primer

<400> SEQUENCE: 31
atcgaccgag cattctagc                                                  19

<210> SEQ ID NO 32
<211> LENGTH: 17
<212> TYPE: DNA
<213> ORGANISM: Artificial
<220> FEATURE:
<223> OTHER INFORMATION: primer

<400> SEQUENCE: 32
tcactctctc accgatc                                                    17

<210> SEQ ID NO 33
<211> LENGTH: 22
<212> TYPE: DNA
<213> ORGANISM: Artificial
<220> FEATURE:
<223> OTHER INFORMATION: primer

<400> SEQUENCE: 33
gttcagtcag cgaatcaatg tc                                              22

<210> SEQ ID NO 34
<211> LENGTH: 20
<212> TYPE: DNA
<213> ORGANISM: Artificial
<220> FEATURE:
<223> OTHER INFORMATION: primer
```

```
<400> SEQUENCE: 34
cagtgccaac ctaaatcctg                                               20

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
ggcccacatg tcatagactt a                                             21

<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36
agcacggcta tgtaagacta ac                                            22

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
agaacgtcat cgacagcatg                                               20

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
tggaccaaaa cttcacttag ta                                            22

<210> SEQ ID NO 39
<211> LENGTH: 19
<212> TYPE: DNA
<213> ORGANISM: Artificial
<220> FEATURE:
<223> OTHER INFORMATION: primer

<400> SEQUENCE: 39
agggcaatgc cgctgctgt                                                19

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
aatgtgcggt gttgatcagc                                               20

<210> SEQ ID NO 41
<211> LENGTH: 17
<212> TYPE: DNA
```

-continued

<213> ORGANISM: Artificial
<220> FEATURE:
<223> OTHER INFORMATION: primer

<400> SEQUENCE: 41
atcagctcgc tgtcgat                                                   17

<210> SEQ ID NO 42
<211> LENGTH: 18
<212> TYPE: DNA
<213> ORGANISM: Artificial
<220> FEATURE:
<223> OTHER INFORMATION: primer

<400> SEQUENCE: 42
tatgccgcag ttcagagc                                                  18

<210> SEQ ID NO 43
<211> LENGTH: 19
<212> TYPE: DNA
<213> ORGANISM: Artificial
<220> FEATURE:
<223> OTHER INFORMATION: primer

<400> SEQUENCE: 43
cttcaggcag atcactcag                                                 19

<210> SEQ ID NO 44
<211> LENGTH: 19
<212> TYPE: DNA
<213> ORGANISM: Artificial
<220> FEATURE:
<223> OTHER INFORMATION: primer

<400> SEQUENCE: 44
aattcgtctc cagttctttt                                                19

<210> SEQ ID NO 45
<211> LENGTH: 17
<212> TYPE: DNA
<213> ORGANISM: Artificial
<220> FEATURE:
<223> OTHER INFORMATION: primer

<400> SEQUENCE: 45
accgccgact actgatc                                                   17

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
atggatggac gacgttacag                                                20

<210> SEQ ID NO 47
<211> LENGTH: 21
<212> TYPE: DNA
<213> ORGANISM: Artificial
<220> FEATURE:
<223> OTHER INFORMATION: primer

<400> SEQUENCE: 47
gtttgtacag aagaagagag t                                              21

RICE PLANT AND METHOD FOR PRODUCING THE SAME

CROSS-REFERENCE TO RELATED APPLICATION

The present application is based upon and claims the benefit of priority from the prior Japanese Patent Application No. 2007-131987 filed on May 17, 2007, the entire contents of which are incorporated herein by reference.

BACKGROUND OF THE INVENTION

1. Field of the Invention

The present invention relates to of a rice plant as a new variety which is obtained by crossing the rice plant varieties "Koshihikari" with "Kasalath" and has improvements in both lodging resistance and grain size, and a method for producing it.

2. Related Art

Koshihikari is a representative rice plant variety of the *Japonica* type rice developed in Japan which has been supported by many consumers as a good taste variety over a half century. Koshihikari, of which the cropping acreage has been increased along with the improvement of cultivation techniques and the intention for better taste of consumers every year, is the variety cultivated most abundantly in Japan. Also, Koshihikari has been progressively cultivated in more northern regions, and thus the area of its cultivation can be expected to be further increased in future.

On the other hand, since Koshihikari is a long culmed variety, it is susceptible to lodging by storm such as typhoon and the early maturing variety is apt to have smaller grains. Therefore, there is a need for an improved variety of Koshihikari which maintains good taste as the characteristic of Koshihikari and has an excellent lodging resistance.

It has hitherto been tried to produce short-culmed varieties, i.e. to dwarf the culm, of rice plants including Koshihikari. As a technique for such attempts, back cross or backcrossing has been conventionally used in which one of parents is crossed again with the F1 hybrid (first filial generation). Particularly, according to continuous backcross in which backcross is carried out continuously, it is possible to produce a congenic line by incorporating a specific gene (a parent carrying the gene being referred to as donor parent), into the genetic background of one of the parents (recurrent parent).

However, the backcross technique is based on the conventional breeding techniques and thus requires a lot of time and labor for substituting genes on a chromosome. Furthermore, it is necessary in the course of backcross to conduct selections repeatedly on the basis of phenotypes, while a lot of experience is required for the selection and it may also be that the results of selection wilt depend on persons who conduct selections. On the other hand, it may be also contemplated to take out a specific gene and to introduce it into a target variety on the basis of the technology of genetic engineering, but the other means which is not based on the technologies of genetic engineering and particularly genetic recombination technique should be examined in consideration of the recent trend of consumers for avoiding genetically modified organisms (GMO).

Thus, efficient methods which can shorten breeding time and be of high reproducibility in relation to the production techniques have been searched with using the conventional breeding techniques without depending on genetic recombination technology. Such an enhancement of the efficiency is also believed to be useful for avoiding the contamination or remaining of the genes other than from the donor parent of the target gene in the other regions on the chromosome. Thus, the so-called marker breeding technique has been paid attention as a method for solving such problems. The marker breeding technique is a technique, which is primarily based on the conventional breeding technique, while the selection is carried out on the basis of the genetic information and technology such as DNA marker in its selection process. Particularly, the decoding of the genome of rice has already been accomplished in relation to rice plant, and investigations are now advanced for utilizing the techniques of genome analysis for the breeding or discrimination of varieties.

For example, multiple genes involved in the heading time have been reported as the result of analysis of gene loci relating to quantitative trait locus (QTL), and it has further been reported that a variety of rice plants exhibiting different heading times could have been developed with DNA markers obtained from such genes (Plant Physiol., 127, 1425-, 200 1). The DNA markers of which breeding methods have been examined include, for example, RFLP (Restriction Fragment Length Polymorphism), RAPD (Random Amplified Polymorphic DNA), AFLP (Amplified Fragment Length Polymorphism), SSR (Simple Sequence Repeat), CAPS (Cleaved Amplified Polymorphic Sequences), and the like.

As regards the technique discriminating the rice variety inclusive of Koshihikari, Japanese Patent Laid-Open Publication No, 2004-65251 discloses a microsatellite marker and a method for distinguishing varieties with it.

Also, International Publication WO 2004/066719 discloses that the lodging resistance of a rice plant has been improved with a marker obtained by the research of single nucleotide polymorphisms (SNPs). However, the variety used as the donor parent in this publication, which exhibits semi-dwarfness, does not affect yield trait, and decorticated grain size was not improved in the improved varieties obtained in practice. That is, in the improved variety described in the publication, while the yield appeared to have been increased in the practical breeding due to the culm shortening and increased heads, the decorticated grain had the size similar to that of Koshihikari or the like and thus the grain size or the improved variety was not increased (please see the column (v) on page 25 and Table 8 of this publication).

Generally, the terms "dwarfness" or "semi-dwarfness" as used in the improved variety mean that the culm length is shortened than normal types and the ear length and particle size of seeds are dwarfed, or that the culm length is shortened without affecting the yield trait including the ear length and the particle size of seeds. The increase of the yield is often observed as the result of stable growing of rice by the improvement of the rice variety to shorten the culm length and avoid lodging, but such dwarfness does not always ensure the increase of the grain size. While larger grain size can be said certainly advantageous. In view of processes including the cooking of rice or the other materials, it can be also said improved marketability for rice which is the staple food in many Asian countries including Japan to have good taste and large grain size.

Thus, a further improved variety of rice other than genetically modified organisms which maintains the good taste of Koshihikari and has an excellent lodging resistance as well as a large grain size is still desired.

SUMMARY OF THE INVENTION

The present inventors unexpectedly have now successfully generated a new rice variety which has large grain size in addition to lodging resistance while keeping the good taste of Koshihikari by continuous backcross with a marker breeding technique which uses "Koshihikari" as a recurrent parent and the Indica type rice variety "Kasalath" as a donor parent. In the process of breeding, the genotype of chromosome was typed with a specific single nucleotide polymorphism (SNP) marker and selected on the basis of the typing. It has not hitherto been described so far as the present inventors know that the chromosomal region and genes involved in these markers relate to the increment of the grain size of the rice plant. The present invention is based on such findings.

Thus, the object of the present invention is to provide a new rice plant which has improvements in both lodging resistance and decorticated grain size while keeping the good taste as a characteristic of Koshihikari. Also, another object of the present invention is to provide a method for construct such a rice plant.

The rice plant according to the present invention is a rice plant obtained by the crossing the rice plant varieties "Koshihikari" with "Kasalath" and having improvement in both lodging resistance and decorticated grain size, wherein said rice plant has on the chromosome any one of base sequences selected from the groups consisting of:

(i) a base sequence of SEQ ID NO: 1,
(ii) a base sequence having at least 80% identity with the base sequence of (i) above, and
(iii) the base sequence of (i) above, in which one or several bases have been deleted, substituted, inserted or added, and wherein the remaining region of the chromosome is composed of chromosomes derived from Koshihikari.

In other words, this rice plant is a non-genetically modified organism (non-GMO).

According to the preferred embodiment of the present invention, said rice plant is obtained by a method comprising the steps of:

(a) crossing Koshihikari as the female plant with Kasalath as the male plant to develop a F1 hybrid (first filial generation),
(b) backcrossing the F1 hybrid thus obtained with Koshihikari followed by the additional backcrossing of at least two times,
(c) typing the genotype of the chromosome of the generation thus obtained with single nucleotide polymorphism (SNP) marker(s), and
(d) selecting an individual plant in which SNP-4 and SNP-5 as the single nucleotide polymorphisms on the chromosome 1 and/or the vicinity thereof are of the Kasalath type and the remaining region is of the Koshihikari type.

More preferably, this method comprises an additional step following the step (d):

(e) typing the progeny with respect to plural SNP sites which are found between the single nucleotide polymorphisms SNP-4 and SNP-5 to select an individual plant on the basis of genotypes thereof.

According to another embodiment of the present invention, a method of cross-breeding, in which the rice plant according to the present invention is used as one of crossing parents is provided.

Furthermore, a method for producing said rice plant variety of which both lodging resistance and decorticated grain size have been improved comprises the following steps of;

(a) crossing Koshihikari as the female plant with Kasalath as the male plant to develop a F1 hybrid,
(b) backcrossing the F1 hybrid thus obtained with Koshihikari followed by the additional backcrossing of at least two times,
(c) typing the genotype of the chromosome of the generation thus obtained with single nucleotide polymorphism (SNP) marker(s), and
(d) selecting an individual plant in which SNP-4 and SNP-5 as the single nucleotide polymorphisms on the chromosome 1 and/or the vicinity thereof are of the Kasalath type and the remaining region is of the Koshihikari type.

Preferably, the method further comprises the above described step (e) following the step (d).

According to the present invention, a rice plant which has the quality of good taste equal to Koshihikari, excellent lodging resistance and in addition large decorticated grain size is provided. Also, the method for producing the rice plant variety according to the present invention utilizes the markers on the basis of the specific SNPs which have been detected in the present invention and thus is easily reproduced by the persons skillful in the art, so that it is possible to construct the rice plant described above easily and certainly within a short period of time. The new variety of the rice plant obtained according to the present invention is generated by the method without depending on the genetic recombination technology and thus has a high safety level, so that it can be also accepted by the consumers who tend to avoid GMO without anxiety.

BRIEF DESCRIPTION OF THE DRAWINGS

FIG. 1 shows diagrammatically chromosome 1 of the rice plant according to the present invention.

FIGS. 3A through 3F show the BAC information for providing markers between Koshihikari and Kasalath.

DETAILED DESCRIPTION OF THE INVENTION

Figure 2:
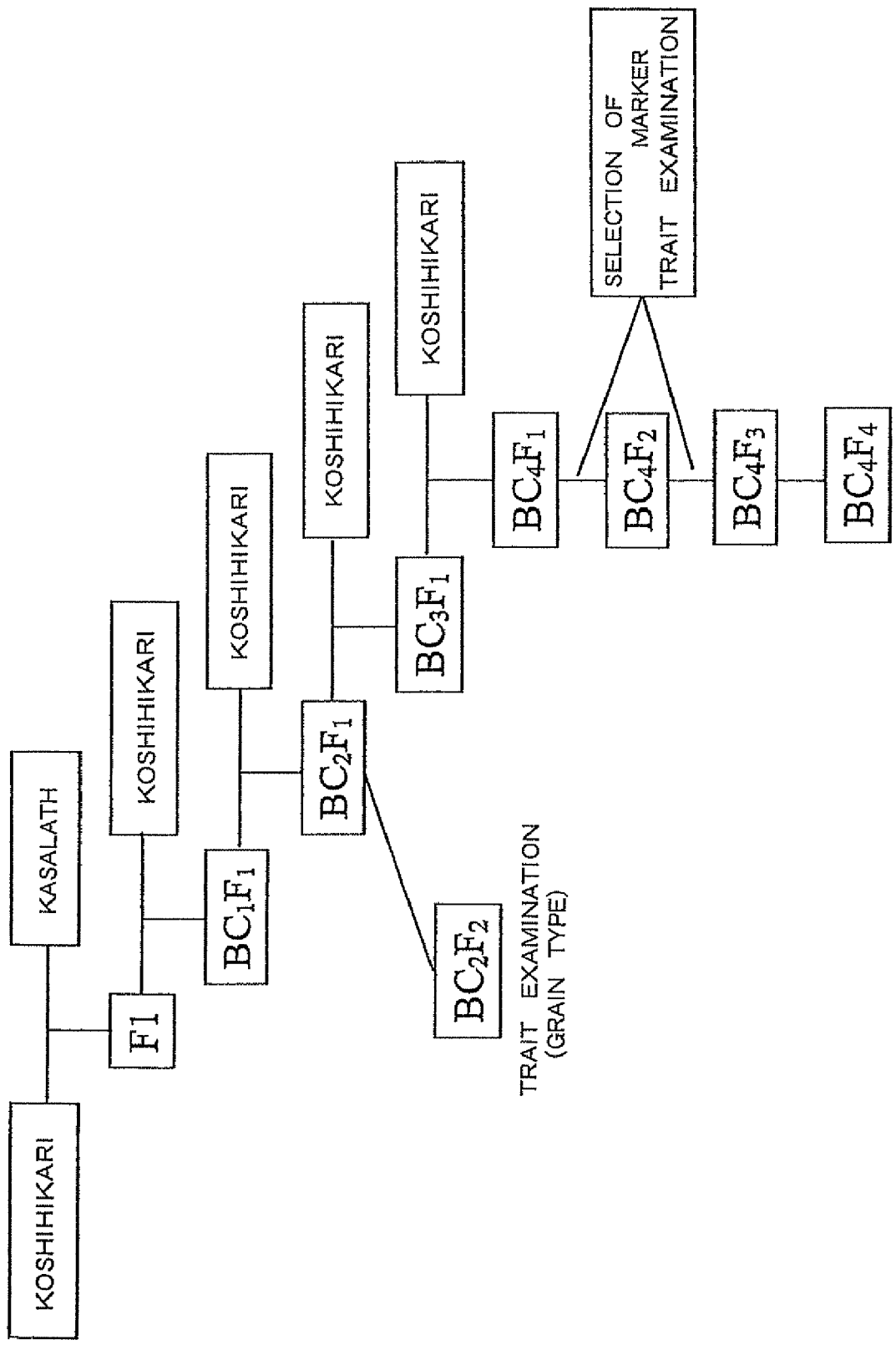
FIG. 2 displays a schematic example of the method for constructing the rice plant according to the present invention.
Figure 3A:
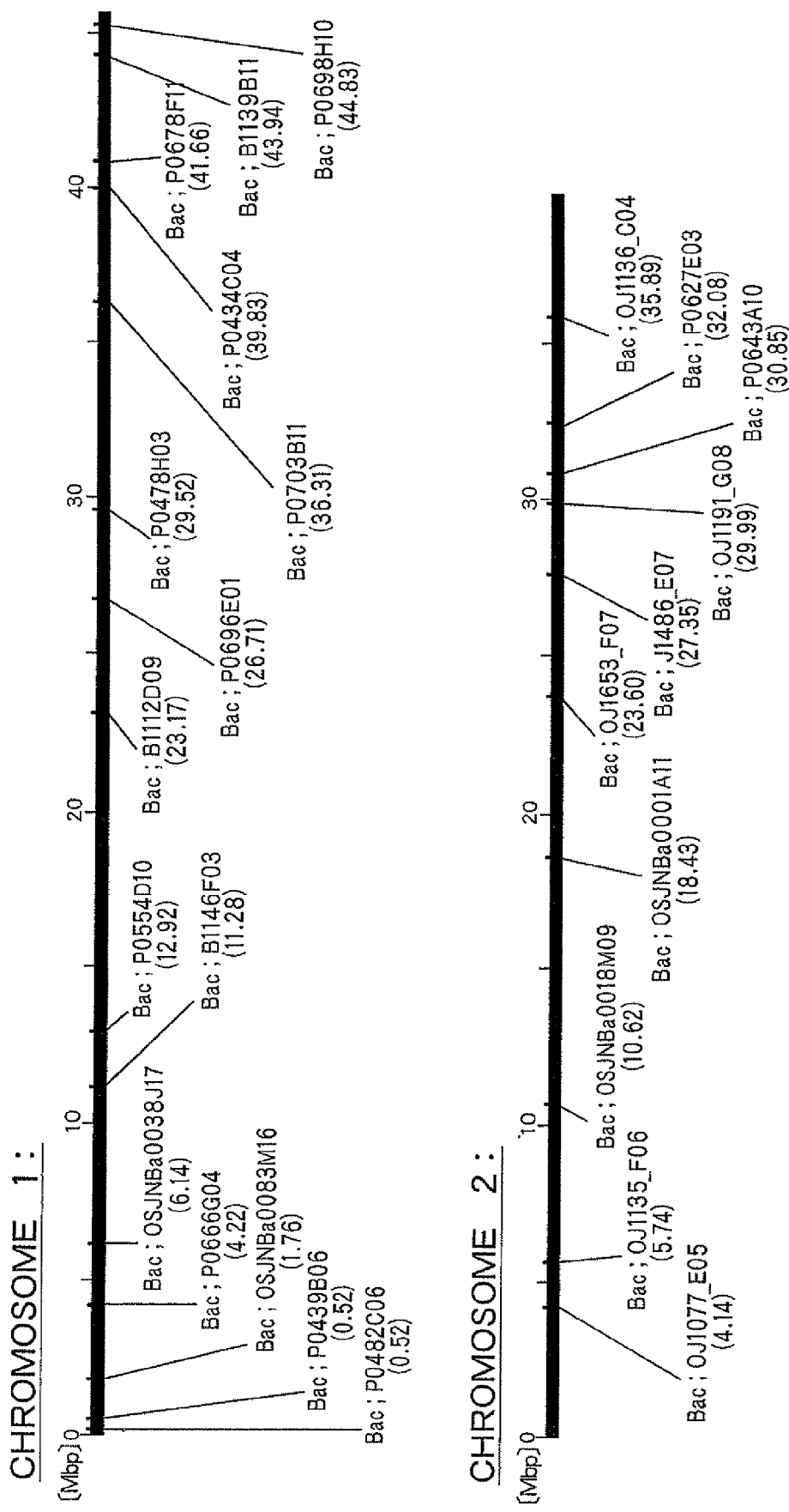
Figure 3C:
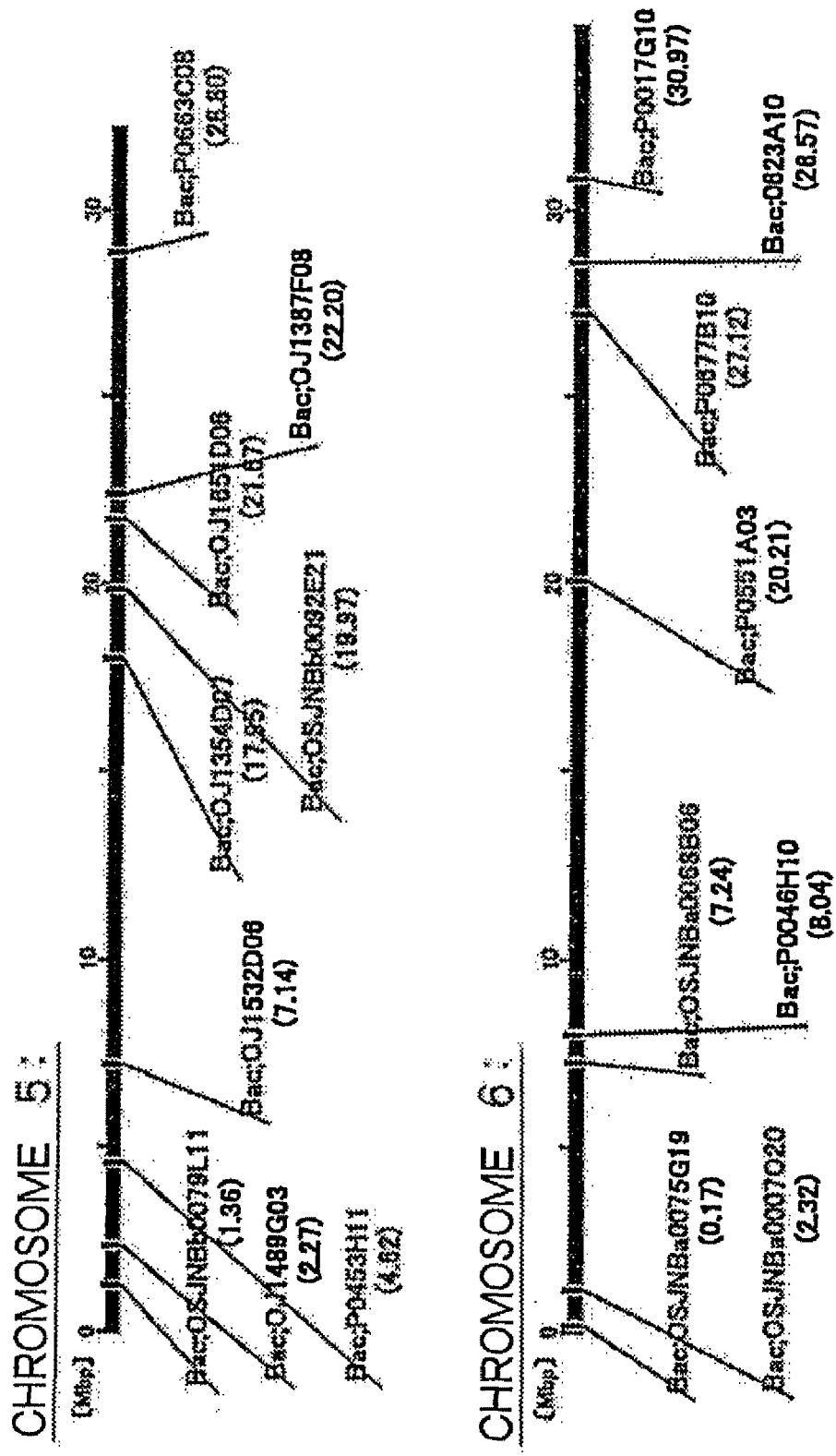
Figure 3D:
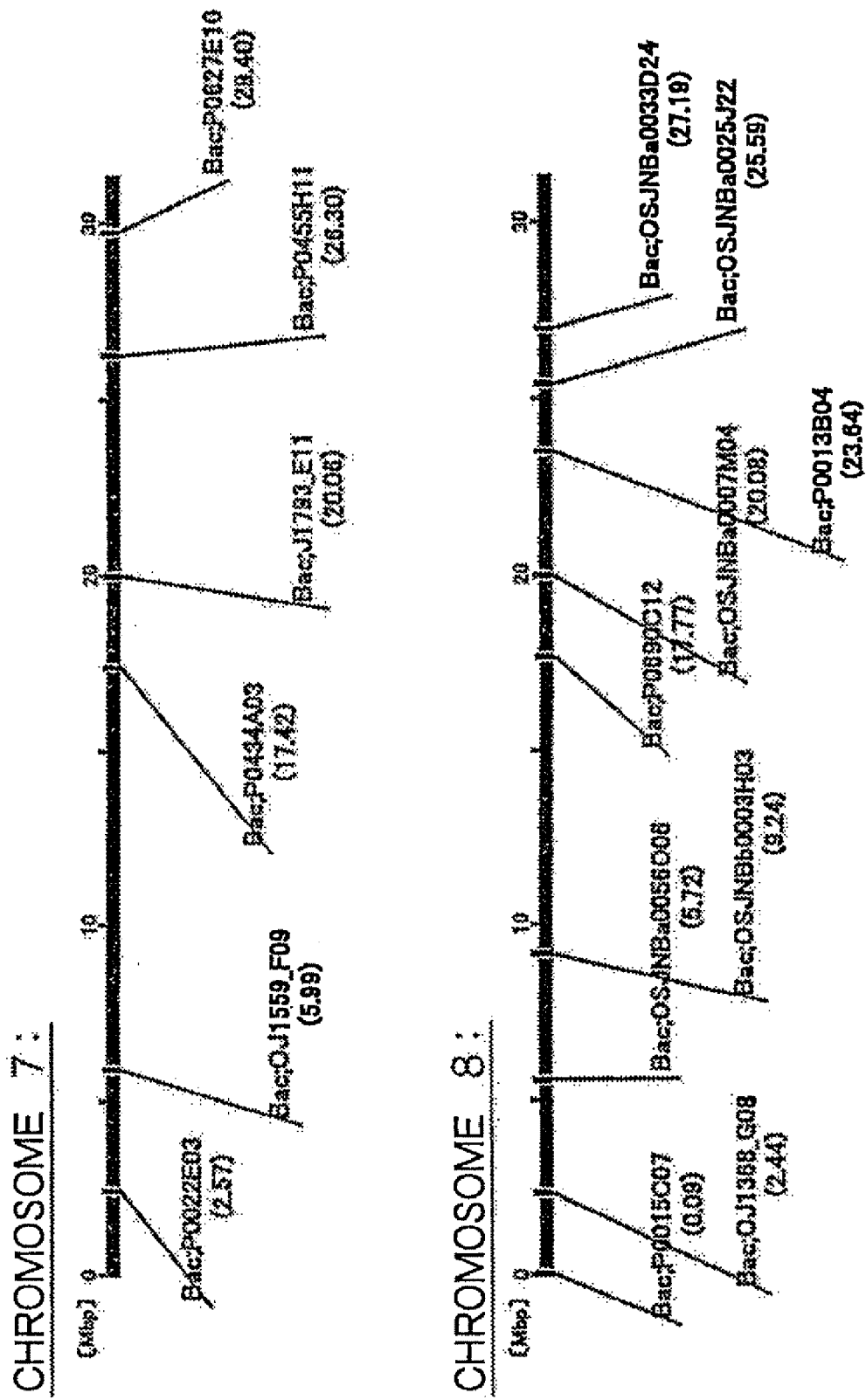
Figure 3E:
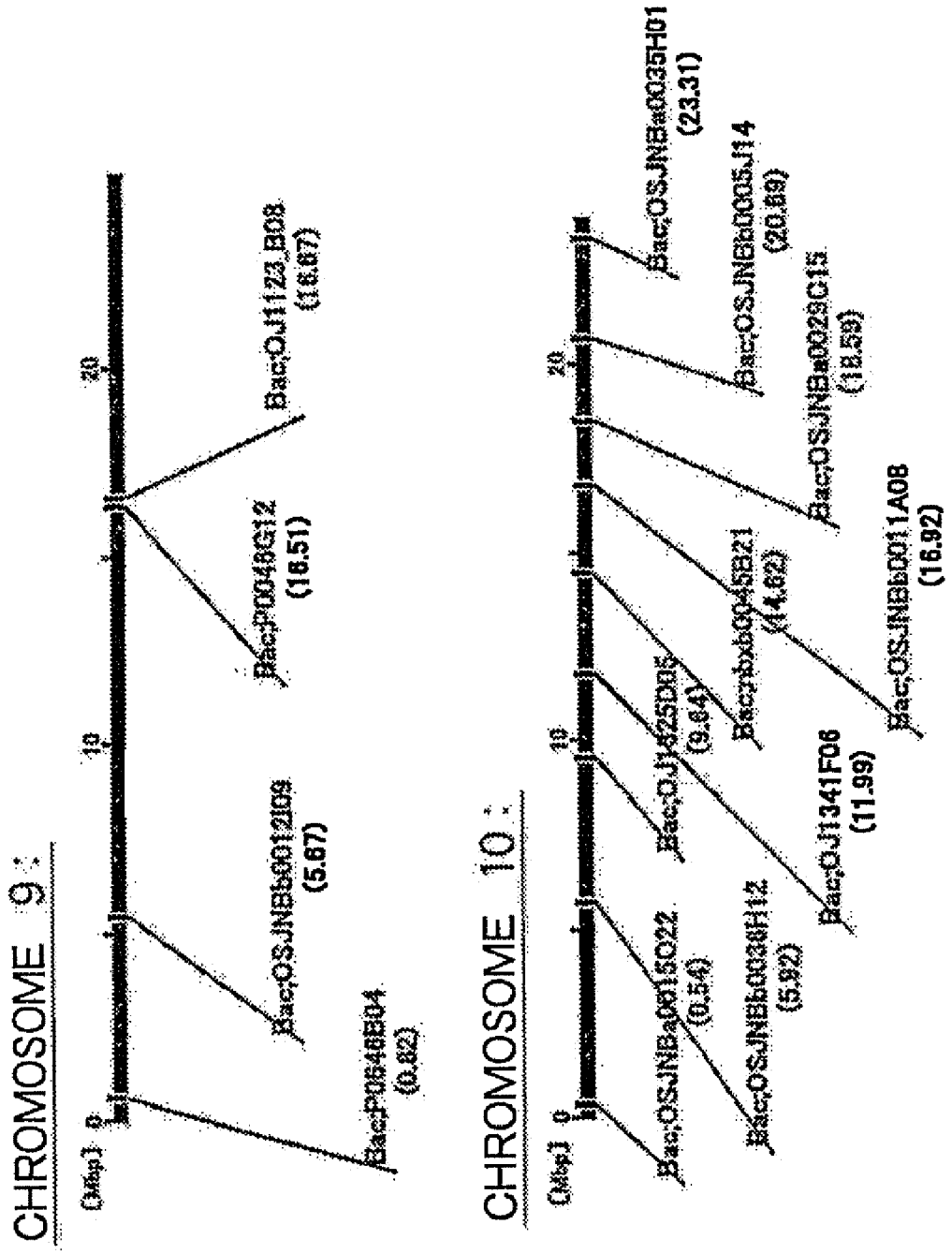
Figure 3F:
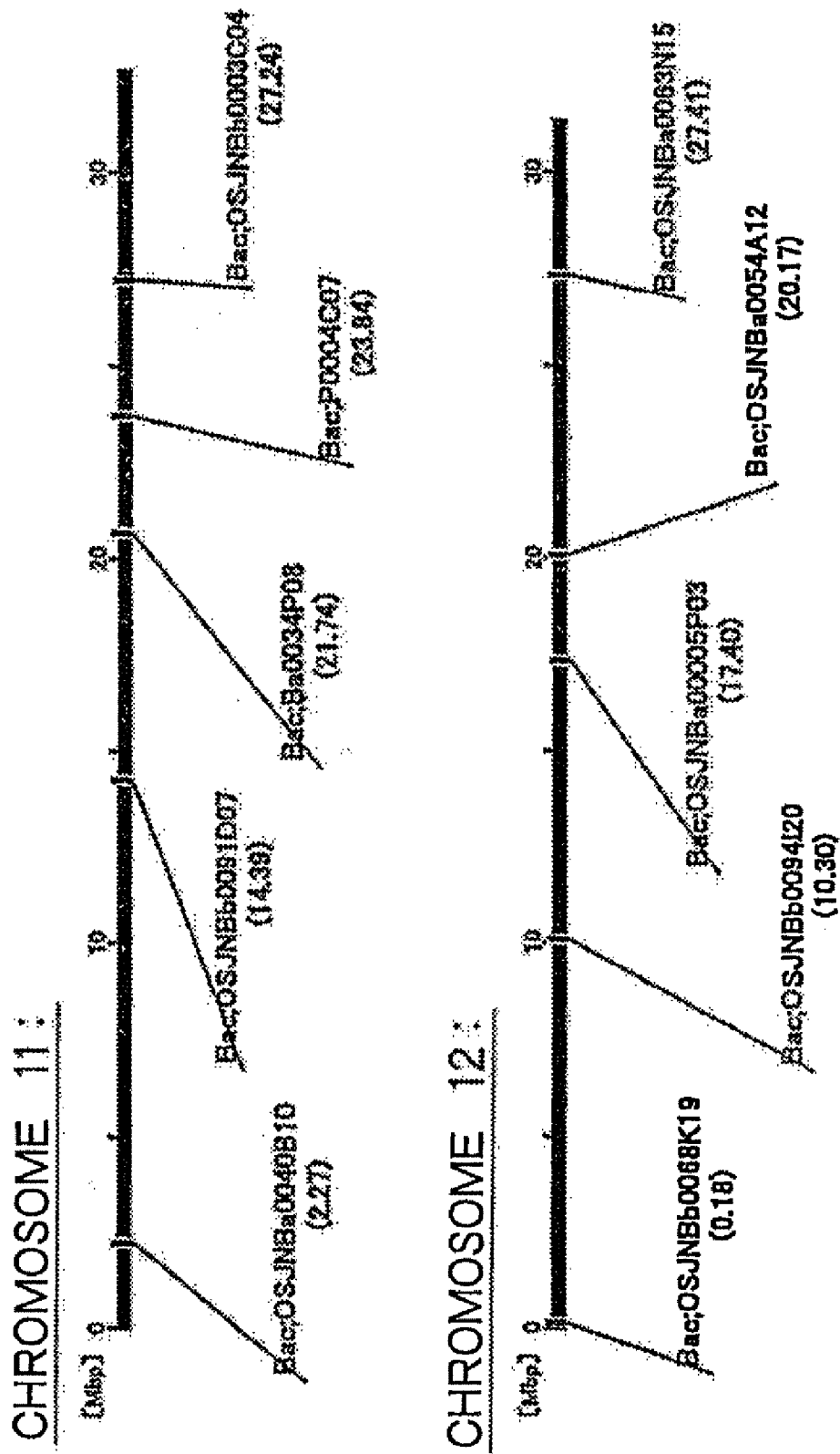

Rice Plant According to the Present Invention

As described above, the rice plant according to the present invention is a rice plant which is obtained by crossing the rice plant varieties "Koshihikari" with "Kasalath" and having improvement in both lodging resistance and decorticated grain size, wherein said rice plant has on the chromosome any one of base sequences selected from the groups consisting of:

(i) a base sequence of SEQ ID NO: 1,
(ii) a base sequence having at least 80% identity with the base sequence of (i) above, and
(iii) the base sequence of (i) above, in which one or several bases have been deleted, substituted, inserted or added, and wherein the remaining region of the chromosome is composed of chromosomes derived from Koshihikari.

As described herein, the phraseology "said rice plant has on the chromosome any one of base sequences selected from . . . , and wherein the remaining region of the chromosome is composed of chromosomes derived from Koshihikari" means that the region corresponding to the base sequence of SEQ ID NO: 1 on the chromosome of Kasalath, preferably the sequence region of SEQ ID NO: 2 on the chromosome of Koshihikari, on the chromosome of Koshihikari, preferably chromosome 1, is substituted by any one of the base sequences selected from (i) to (iii) and that the chromosome of Koshihikari is maintained with respect to the remaining region. In other words, the region on the chromosome is basically derived from Koshihikari except that a part of the chromosome of Koshihikari is substituted by any one of the base sequences selected from (i) to (iii). Preferably, the gene comprising the base sequence represented by SEQ ID NO: 1 is derived from Kasalath.

In this connection, the chromosome 1 of the rice plant according to the present invention is believed in such a state that illustrated diagrammatically in FIG. 1.

The case having the base sequence of (ii) or (iii) described above means inclusive of the cases that mutation in the base sequence represented by SEQ ID NO. 1 is caused by some reasons without depending on artificial techniques including genetic recombination technology, mutation is caused in Kasalath used as the donor parent, or a Kasalath relative species is used.

In this connection, the base sequence of (ii) or (iii) is the one which exhibits substantially the same activity as the above described base sequence of (i) when it is positioned in the fixed region of the chromosome of a rice plant. Namely, the base sequence of (ii) or (iii) is the one which can afford the rice plant both the desired lodging resistance and the improved decorticated grain size by positioning it in the fixed region of the chromosome of a rice plant.

The base sequence of (ii) described above is not particularly limited as far as it is identical to the base sequence of (i) in a level of 80% or more. It is a base sequence having an identity of preferably 85% or more, more preferably 90% or more, further preferably 95% or more, further more preferably 98% or more, particularly 99% or more with said base sequence of (i). In this connection, the value of the "identity" may be the one calculated with a homology search program well known to persons skillful in the art, and it may be calculated, for example, by using the default (initial set) parameter in the homology algorism BLAST (Basic Local Alignment Search Tool) at the National Center for Biotechnology Information (NCBI).

In the base sequence of (iii) described above, the number of bases which may be deleted, substituted, inserted or added is, for example, in the range of 1 to 2400, preferably 1 to 1200, more preferably 1 to 600, further preferably 1 to 200, further more preferably 1 to 100, further preferably 1 to 50, even more preferably 1 to 10, still more preferably 1 to 5, and particularly 1 to 2.

According to the preferred embodiment of the present invention, the base sequence of (iii) above may be substituted according to the condition that the amino acid sequence encoded by the base sequence may be conservatively substituted. The term "conservative substitution" used herein refers to substitutions of one or several amino acid residues with other chemically similar amino acid residues without substantially altering the activity of a peptide. For example, such substitution includes the cases of substituting a hydrophobic residue by another hydrophobic residue, a polar residue by another polar residue having the equivalent electric charge, and the like. The amino acids having the similar functions which can be used for such substitution are well known in the art. Specific examples for the non-polar (hydrophobic) amino acids include alanine, valine, isoleucine, leucine, proline, tryptophan, phenylalanine, methionine, and the like. Examples for the polar (neutral) amino acids include glycine, serine, threonine, tyrosine, glutamine, asparagine, cysteine, and the like. Examples for the (basic) amino acids having positive charges include arginine, histidine, lysine and the like. Also, examples for the (acidic) amino acids having negative charges include aspartic acid, glutamic acid, and the like.

The phenotype of the rice plant according to the present invention has the following feature: the plant type is an intermediate type, the stem length is medium, the stem thickness is slightly thick, the stem softness is slightly soft, and the erectness of flag leaf is medium. The panicle length is slightly short, the number of ears is medium, and the grain forming density is slightly dense. The color of lemma is light gold, the color of tip of lemma is light gold—yellow, the presence and number of awns are very many, and the length of awns is medium. The shape of decorticated grain is medium, the decorticated grain size is medium, the apparent quality of decorticated grain is lower medium, and the luster is slightly large. The times of heading and maturity are late of early, the sprouting resistance is strong, and the lodging resistance is very weak. In this connection, the indices described above was in comparison with Koshihikari as the control, and, if appropriate, evaluated according to the table of characteristics and the examination guideline published from the Ministry of Agriculture, Forestry and Fisheries (MAFF) in Japan. In this connection, the table of characteristics and the examination guideline by the MAFF basically follow the test guideline for DUS tests (for rice) published from the UPOV union (International Union for the Protection of New varieties of Plants).

According to another embodiment of the present invention, a method for cross-breeding a rice plant, in which the rice plant according to the present invention is used as one of parents. Another parent may be either of the rice plant varieties of Japonica or Indica type without limitation. Thus, it is possible to use well known varieties such as Koshihikari, Sasanishiki; Akitakomachi, Nipponbare, Haenuki, Hitomebore, Milky Queen, Yamadanishiki, Hinohikari, Kinuhikari, Kirara 397, Habataki, and the like as another parent. It is possible to obtain a hybrid variety having the lodging resistance equivalent to the rice plant according to the present invention and the improved decorticated grain size by the cross-breeding method.

According to another embodiment of the present invention, there is provided a rice plant which is obtained by cross-breeding the rice plant according to the present invention as one of the parents. It can be said that the rice plant described herein means the F1 hybrid (the first filial generation F1). Alternatively, when the rice plant described herein means a progeny from F1 generation in the cross-breeding, said rice plant has improvements in the lodging resistance and the decorticated grain size at least in the same level as the above described rice plant according to the present invention, Produce of the Rice Plant The new rice plant according to the present invention is obtained by the crossing of the varieties "Koshihikari" and "Kasalath".

Preferably, it is obtained by the method comprising the following steps:

(a) crossing Koshihikari as the female plant with Kasalath as the male plant to develop a F1 hybrid, (b) backcrossing the F1 hybrid thus obtained with Koshihikari followed by the additional backcrossing of at least two times, (c) typing the genotype of the chromosome of the generation thus obtained with single nucleotide polymorphism (SNP) marker(s), and (d) selecting an individual plant in which SNP-4 and SNP-5 as the single nucleotide polymorphisms on the chromosome 1 and/or the vicinity thereof are of the Kasalath type and the remaining region is of the Koshihikari type.

In this connection, the term "backcrossing" means that a recurrent parent and a donor parent are crossed to give crossing progenies (F1 hybrid), from which an individual for the crossing of the next generation is selected under a certain condition, and the recurrent parent is crossed again with the individual thus selected to repeat such procedures. According to such crossing procedures, it is possible to obtain finally a congenic plant strain comprising the target gene locus of a homozygous donor parent and the remaining chromosome region which is composed of the chromosomes derived from a recurrent parent.

In the present invention, the genotype of the chromosome in the selection of a crossing progeny is typed with a SNP marker(s) to select an individual used for the crossing of the next generation on the basis of the genotype of the chromosome. The selection is typically carried out during the translocation from the form of embryo to sprouting time to an adult plant.

As described herein, the term single nucleotide polymorphism (SNP) means a polymorphism in which a base in the base sequence has been mutated, and in the present invention, it means the point mutation between "Koshihikari" as the recurrent parent and "Kasalath" as the donor parent. In this connection, single nucleotide polymorphism (SNP) in the present invention means that, in addition to the polymorphism by the substitution of a base, the insertion, deletion or addition of a base can be also included.

The summary of the method for constructing the rice variety according to the present invention is diagrammatically shown in FIG. 2 and now described more particularly as follows.

Steps (a) and (b):

The seeds of Koshihikari (recurrent parent) and Kasalath (donor parent) are provided and dipped into water for a few days, e.g., two days, at a temperature of about 30° C. to force germination. These seeds are cultivated in a greenhouse and put forth ears for crossing. The crossing was carried out with Koshihikari as a female plant and Kasalath as a male plant, and usually the female plant is castrated prior to pollination. It is possible to reach a ripening stage within about 3 to 4 weeks after the crossing procedure and to get the seeds of the first filial generation F1 (the F1 hybrid).

Next, the seeds of the first filial generation F1 thus obtained were germinated, cultivated and put forth ears in the same manner as the above described parents. Then, Koshihikari which has eared in the same manner as described above was crossed for the first backcrossing. In this connection, the crossing was carried out with the first filial generation F1 as a female plant and Koshihikari as a male plant to get the BC1F1 generation. The seeds of the BC1F1 generation thus obtained were treated in the same manner as described above, and the next crossing was carried out with the BC1F1 generation as a female plant and Koshihikari as a male plant, followed by repeated backcrossing.

The backcrossing is repeated at least twice, preferably at least thrice, inclusive of the backcrossing described above. When the generation obtained has become BC2F1 generation or later generations (preferably, BC3F1 generation), the genotype of the chromosome of the generation obtained is typed with an SNP marker.

In order to type the genotype, it is desirable to set up preliminarily SNP markers which can be used between Koshihikari (recurrent parent) and Kasalath (donor parent) over the whole chromosome.

At this point, the genomic DNA from "Koshihikari" and "Kasalath" can be extracted, e.g., by the CTAB method (Murray, M. G, et al., Nucleic Acids Res., 8, 4321-4325, 1980, etc.).

The SNP marker can be set up with base sequence databases such as rice EST or BAC disclosed by Rice Genome Research Program (RGP) or well known marker information such as the BAC information for setting up the marker between Koshihikari and Kasalath disclosed in the web home page of Inplanta Innovations Inc. (FIG. 3).

SNP can be detected, for example, by the AcycloPrime-FP method (Genome Research, 9, 492-498, 1999), the PCR-SSCP (single-strand conformation polymorphism) method (Genomics, January 1, 12(1), 139-146, 1992; Oncogene, August 1, 6(8), 1313-1318, 1991; PCR Methods Appl., April 1, 4(5), 275-282, 1995), the TaqMan PCR method ("Strategy of SNP Gene Polymorphism", Kenichi Matsubara & Yoshiyuki Sakaki, Nakayama Shoten Co., Ltd., pp, 94-105), the Invader method ("Strategy of SNP Gene Polymorphism", Kenichi Matsubara & Yoshiyuki Sakaki, Nakayama Shoten Co., Ltd. pp. 94-105), the pyrosequencing method (Anal. Biochem., 10, 103-110, 2000), the MALDI-TOF MS method (Trends Biotechnol., 18, 77-84, 2000), the DNA array method ("Strategy of SNP Gene Polymorphism", Kenichi Matsubara & Yoshiyuki Sakaki, Nakayama Shoten Co., Ltd., pp. 128-135), and the like.

In the present, invention, the SNP marker are set up so that a plurality of SNP markers are present corresponding to one chromosome on the basis of the information described above. In the present invention, the available SNP which is detected for the whole genome includes 89 SNPs listed in Table 1. In this connection, the position of the SNP represents the position of TIGR (The Institute for Genomic Research) on the database (TIGR RICE Pseudomolecules).

TABLE 1

| SNP # | Chromosome No. | position | Detected polymorphism (Koshihikari/Kasalath) |
|---|---|---|---|
| SNP-1 | 1 | 590,339 | C/T |
| SNP-2 | 1 | 2,275,275 | C/G |
| SNP-3 | 1 | 6,522,242 | T/C |
| SNP-4 | 1 | 11,026,011 | T/G |
| SNP-101 | 1 | 13,873,241 | C/G |
| SNP-102 | 1 | 14,019,919 | A/G |
| SNP-103 | 1 | 14,429,234 | G/T |
| SNP-104 | 1 | 14,440,300 | C/G |
| SNP-105 | 1 | 14,468,824 | G/C |
| SNP-5 | 1 | 17,803,741 | T/G |
| SNP-6 | 1 | 22,682,204 | C/T |
| SNP-7 | 1 | 27,840,561 | G/A |
| SNP-8 | 1 | 33,256,185 | C/T |
| SNP-9 | 1 | 38,966,202 | T/C |
| SNP-10 | 1 | 42,768,125 | A/G |
| SNP-11 | 2 | 4,228 | A/G |
| SNP-12 | 2 | 2,010,334 | C/G |
| SNP-13 | 2 | 6,001,543 | A/G |
| SNP-14 | 2 | 11,826,616 | A/T |
| SNP-15 | 2 | 16,115,080 | A/T |
| SNP-16 | 2 | 22,086,348 | T/G |
| SNP-17 | 2 | 26,519,366 | G/C |
| SNP-18 | 2 | 32,760,299 | A/T |

TABLE 1-continued

| SNP名 | Chromosome No. | position | Detected polymorphism (Koshihikari/Kasalath) |
|---|---|---|---|
| SNP-19 | 2 | 34,879,166 | G/C |
| SNP-20 | 3 | 698,220 | T/C |
| SNP-21 | 3 | 1,465,820 | T/A |
| SNP-22 | 3 | 6,252,925 | G/A |
| SNP-23 | 3 | 11,073,623 | T/A |
| SNP-24 | 3 | 18,234,158 | T/A |
| SNP-25 | 3 | 24,639,787 | C/T |
| SNP-26 | 3 | 30,021,442 | C/G |
| SNP-27 | 3 | 35,945,011 | T/C |
| SNP-28 | 4 | 218,809 | A/T |
| SNP-29 | 4 | 2,471,151 | G/A |
| SNP-30 | 4 | 6,456,488 | C/T |
| SNP-31 | 4 | 11,949,079 | T/C |
| SNP-32 | 4 | 17,166,348 | T/C |
| SNP-33 | 4 | 23,043,128 | T/C |
| SNP-34 | 4 | 29,103,653 | C/G |
| SNP-35 | 4 | 34,498,729 | C/T |
| SNP-36 | 5 | 40,031 | A/G |
| SNP-37 | 5 | 2,258,619 | A/T |
| SNP-38 | 5 | 6,302,514 | T/C |
| SNP-39 | 5 | 12,908,872 | G/C |
| SNP-40 | 5 | 18,878,114 | T/C |
| SNP-41 | 5 | 23,309,954 | A/G |
| SNP-42 | 5 | 28,530,312 | T/C |
| SNP-43 | 6 | 260,320 | T/C |
| SNP-44 | 6 | 2,186,456 | C/A |
| SNP-45 | 6 | 5,904,224 | T/G |
| SNP-46 | 6 | 11,834,155 | T/A |
| SNP-47 | 6 | 18,785,728 | C/A |
| SNP-48 | 6 | 24,739,275 | C/T |
| SNP-49 | 6 | 29,975,546 | C/A |
| SNP-50 | 7 | 260,864 | T/A |
| SNP-51 | 7 | 2,632,936 | G/T |
| SNP-52 | 7 | 7,936,831 | A/G |
| SNP-53 | 7 | 13,302,019 | A/G |
| SNP-54 | 7 | 18,571,959 | C/T |
| SNF-55 | 7 | 24,176,601 | C/G |
| SNF-56 | 7 | 29,468,003 | G/A |
| SNP-57 | 8 | 195,223 | T/C |
| SNP-58 | 8 | 2,203,630 | A/G |
| SNP-59 | 8 | 5,276,855 | A/G |
| SNP-60 | 8 | 11,498,754 | G/T |
| SNP-61 | 8 | 17,423,651 | T/C |
| SNP-62 | 8 | 23,067,294 | G/T |
| SNP-63 | 8 | 28,139,529 | T/C |
| SNP-64 | 9 | 22,021 | C/A |
| SNP-65 | 9 | 3,066,192 | T/A |
| SNP-66 | 9 | 6,999,573 | A/C |
| SNP-67 | 9 | 12,344,807 | G/A |
| SNP-68 | 9 | 17,880,593 | T/C |
| SNP-69 | 9 | 20,732,643 | T/C |
| BNP-70 | 10 | 94,506 | G/C |
| SNP-71 | 10 | 2,541,199 | A/G |
| SNP-72 | 10 | 7,069,227 | T/G |
| SNP-73 | 10 | 12,259,238 | T/C |
| SNP-74 | 10 | 17,555,159 | T/C |
| SNP-75 | 10 | 22,686,557 | A/G |
| SNP-76 | 11 | 827,222 | G/A |
| SNP-77 | 11 | 2,489,967 | T/C |
| SNP-78 | 11 | 7,881,526 | A/T |
| SNP-79 | 11 | 12,851,395 | G/T |
| SNP-80 | 11 | 18,135,403 | A/G |
| SNP-81 | 11 | 24,056,275 | A/G |
| SNP-82 | 11 | 27,755,587 | G/T |
| SNP-83 | 12 | 322,928 | G/C |
| SNP-84 | 12 | 3,185,499 | C/T |
| SNP-85 | 12 | 7,519,475 | T/C |
| SNP-86 | 12 | 12,334,210 | A/G |
| SNP-87 | 12 | 17,881,114 | T/C |
| SNP-88 | 12 | 23,294,647 | G/T |
| SNP-89 | 12 | 27,011,209 | A/G |

Also, the genome PCR primer sets (5'-side primer, 3'-side primer) corresponding to the SNP markers are shown in Table 2.

TABLE 2

| SNP | Common name | Chromosome No. | position | Detected polymorphism (Koshihikari/Kasalath) | PCR primer-1 | PCR primer-2 | SNP marker | SEQ ID NOS (of the primers and marker in order) |
|---|---|---|---|---|---|---|---|---|
| SNP-1 | BB-77 | 1 | 530,339 | C/T | GTAGGTGCAAAGTGTGCC | CAGCATGGTGTACCAGGA | CTCTTTAGGGTGTTACCATG | 3, 4, 5 |
| SNP-2 | AB-56 | 1 | 2,275,275 | C/G | GGAATTCAGAGACAACATGG | GCTTCAGTGTTGTGTGATTCTG | TTCTTCCTCCAGTACCAGAT | 6, 7, 8 |
| SNP-3 | CA-77 | 1 | 6,522,242 | T/C | CCTAATGGGCCGAATTTATAACG | GCGAAAGGCGAGGTTGATG | CAAAGTAATTTGGGATCTTTAC | 9, 10, 11 |
| SNP-4 | AB-92 | 1 | 11,026,011 | T/G | TCCCTGCTGCTAGGATCTTG | ATCCATCAAGTCAGCAGGTG | GCTGTGAATGGATGCCAA | 12, 13, 14 |
| SNP-101 | HSNP-1 | 1 | 13,873,241 | C/G | CTTGTAACAGGTGTCCTCGA | CAATAACAGCCTGCAACGAAC | GGCTGACCAACAAAAGACA | 15, 16, 17 |
| SNP-102 | HSNP-2 | 1 | 14,019,919 | A/G | GAAACGGGATGTCAACACAG | GACAGCTTGAACAATTGACTGG | CACAACTCACAAGTAACAAAC | 18, 19, 20 |
| SNP-103 | HSNP-3 | 1 | 14,429,234 | G/T | GATTCGAACCCATGACCTAG | GACACACCAACGTTCAGCTC | TTCGAACCCATGACCTAGCG | 21, 22, 23 |
| SNP-104 | HSNP-4 | 1 | 14,440,300 | C/G | CTGAGGATGAACCTACAATGG | CGTGCTGCTAATTACTCATGC | AGTAATGGATCCAGGAACATG | 24, 25, 26 |
| SNP-105 | HSNP-5 | 1 | 14,468,824 | G/C | CCGTGTTTTTCGATTGGCAC | GATGATTAGCTGTCCTGTCC | CTTTCTTGTTGGTTGTAGTAGCTA | 27, 28, 29 |

TABLE 2 -continued

| SNP | Common name | Chromosome No. | position | Detected polymorphism (Koshihikari/ Kasalath) | PCR primer-1 | PCR primer-2 | SNP marker | SEQ ID NOS (of the primers and marker in order) |
|---|---|---|---|---|---|---|---|---|
| SNP-5 | BC-08 | 1 | 17,803,741 | T/G | GAGGCCATTCTC GCAAC | ATCGACCGAGCA TTCTAGC | TCACTCTCTCAC CGATC | 30, 31, 32 |
| SNP-6 | AC-21 | 1 | 22,682,204 | C/T | GTTCAGTCAGCGA ATCAATGTC | CAGTGCCAACCT AAATCCTG | GGCCCACATGTC ATAGACTTA | 33, 34, 35 |
| SNP-7 | AC-42 | 1 | 27,840,561 | G/A | AGCACGGCTATG TAAGACTAAC | AGAACGTCATCG ACAGCATG | TGGACCAAAACT TCACTTAGTA | 35, 36, 37 |
| SNP-8 | AC-70 | 1 | 33,256,185 | C/T | AGGGCAATGCCG CTGCTGT | AATGTGCGGTGT TGATCAGC | ATCAGCTCGCTG TCGAT | 38, 39, 40 |
| SNP-9 | AE-88 | 1 | 38,966,202 | T/C | TATGCCGCAGTT CAGAGC | CTTCAGGCAGAT CACTCAG | AATTCGTCTCCA GTTCTTT | 41, 42, 43 |
| SNP-10 | AE-84 | 1 | 42,768,125 | A/G | ACCGCCGACTAC TGATC | ATGGATGGACGA CGTTACAG | GTTTGTACAGAA GAAGAGAGT | 45, 46, 47 |

Steps (c) and (d):

In the typing of the genotype, the seeds of the generation to be typed are sowed, the leaves of seedlings are collected about 7 to 14 days after sowing, and the genomic DNA is extracted from the leaves by the simple genome extraction method (Lisa Monna, et al., DNA Research, 9, 11-17, 2002).

First, the region containing SNPs is amplified by PCR with the genomic DNAs from the both lines, and after the confirmation of amplification by agarose gel electrophoresis, the amplified products are treated with enzymes to decompose the remaining primers and dephosphorylate mononucleotides. Next, the SNP primers constructed at single base prior to the SNPs and two fluorescence labeled dideoxynucleotides (two of ddATP, ddCTP, ddGTP and ddCTP) corresponding to the respective SNPs are subjected to the single base extension reaction with a PCR product as a template (AcycloPrime reaction). The reaction product exhibits a fluorescence polarization degree corresponding to the respective SNPs (Chen, X. et al., Genome Res., 9, 492-498, 1999), and thus the fluorescence polarization degree is measured for the typing of genotype. Herein, the term "typing" of genotype means to determine or judge whether the base species at the SNP site is of the Koshihikari type or of the Kasalath type.

The genotype of the chromosome at the stage of the above described BC2F1 generation or later (preferably, BC3F1 generation) was typed, and an individual in which SNP-4, SNP-5 and/or the vicinity thereof on the chromosome are of the Kasalath type and the remaining region is of the Koshihikari type is selected on the basis of the typing. In this connection, the term vicinity means SNP-3 and/or SNP-6 which are adjacent to SNP-4 and SNP-5.

The individual selected above (the selected BC2F1 generation or later (preferably, BC3F1 generation)) is further subjected to backcrossing, the genotype of the chromosome is typed in this generation (BC3F1 generation or later (preferably BC4F1 generation)), and an individual in which only SNP-4 and SNP-5 on the chromosome are of the Kasalath type or only SNP-4 and SNP-5 and SNP-3 and/or SNP-6 as the vicinity thereof are of the Kasalath type is selected.

Step (e):

According to the preferred embodiment of the present invention, a plurality of SNP sites present between the single nucleotide polymorphisms SNP-4 and SNP-5 are typed after the above described step for further step of select an individual on the basis of the genotypes.

Among the SNPs which have been set up according to the present invention, SNP-101, SNP-102, SNP-103, SNP-104 and SNP-105 are further detected between SNP-4 and SNP-5. Thus, "a plurality of SNP sites present between the single nucleotide polymorphisms SNP-4 and SNP-5" preferably refer to SNP-101, SNP-102, SNP-103, SNP-104 and SNP-105.

The next generation (preferably BC4F2 generation) is obtained from the generation obtained above (BC3F1 generation or later (preferably BC4F1 generation)) and is subjected to raising of seedlings with about 1000 individuals, from which the individuals SNP-101, SNP-102, SNP-104 and SNP-105 exhibit the genotypes of Koshihikari-homotype, heterotype, heterotype and heterotype, or heterotype, heterotype, heterotype and Koshihikari-homotype, respectively, are selected.

Next, a later progeny (preferably BC4F3 generation) is obtained from of the selected generation, and is subjected to raising of seedlings with about 1000 individuals, from which the individuals SNP-101, SNP-102, SNP-104 and SNP-105 exhibit the genotypes of Koshihikari-homotype, heterotype, heterotype and Koshihikari-homotype, respectively, are selected.

Furthermore, a still later progeny (preferably BC4F4 generation) is obtained from of the selected generation, and is subjected to raising of seedlings with about 20 individuals, from which the individuals SNP-101, SNP-102, SNP-103, SNP-104 and SNP-105 exhibit the genotypes of Koshihikari-homotype, Kasalath-homotype, Kasalath-homotype and Koshihikari-homotype, respectively, are selected.

The target rice plant can be obtained by these selections. The fixed line thus obtained is cultivated in the field for detailed character examination, whereby it can be confirmed that the cultivated strain has not only large grain size but also short culm length.

It has been described above that the rice plant according to the present invention has any one of base sequences selected from the (i) to (iii) on the chromosome and the remaining region of the chromosome is composed of chromosomes derived from Koshihikari, and it may be readily confirmed according to the typing with markers based on the SNP information presented in the following examples by persons skilled in the art that the rice plant bred according to the present invention has the base sequence described above and the remaining chromosome region is composed of the chromosomes derived from Koshihikari. It may also be confirmed by sequencing the certain gene region on the chromosome 1 and typing with the SNP markers. Alternatively, it may be also confirmed by sequencing the certain gene region on the chromosome 1 and typing with a marker such as AFLP (Amplified Fragment Length Polymorphism) with which whole genome can be searched.

EXAMPLES

The present invention will be described in detail in the following with examples which are not intended to limit the invention.

Example 1

Detection and Setting up of SNP Marker

In the present invention, 89 SNPs which can be used between the variety "Koshihikari" as the recurrent parent and the variety "Kasalath" as the donor parent were detected as described below (Table 1) for setting up the SNP markers (Table2).

Koshihikari and Kasalath were provided, and these mature leaves were subjected to the genomic DNA extraction, for example, with the CTAB method. Next, SNP sites were first searched by comparing the Japonica type rice (variety: "Nipponbare") and the Indica type rice (variety: "9311", BGI (Beijing Genomics Institute)) on the basis of the published databases for designing primers (about 300) in order to detect these SNPs. Genomic PCR primer sets (5'-side primer, 3'-side primer) for the SNP markers were prepared from the primers obtained, and used for the amplification of the region containing the SNPs with each genomic DNA of "Koshihikari" and "Kasalath" extracted above as a template. The amplified product was treated with alkaline phosphatase and exonuclease I to decompose the remaining primers and dephosphorylate mononucleotides. The single base extension reaction (AcycloPrime reaction) with the SNP primers and two fluorescence labeled dideoxynucleotides (two of ddATP, ddCTP, ddGTP and ddCTP) corresponding to the respective SNPs was carried out with the PCR product as a template with use of an AcycloPrime-FP SNPs Detection Kit (PerkinElmer Life Sciences). The fluorescence polarization degree of the reaction product was measured by a multilabel counter ARVO 1420-043 (PerkinElmer Life Science) to determine the base of the SNP site (genotype). The result of the search was combined with a new constructed marker with the well known base sequence database of rice plant to make 89 SNP markers which exhibit polymorphism between "Koshihikari" and "Kasalath".

Furthermore, "Koshihikari" and "Kasalath" were practically sequenced on the basis of the published information of "Nipponbare" to detect SNPs. Based on the obtained information, the primers were designed to make the markers (SNP-101, SNP-102, SNP-103, SNP-104 and SNP-105).

Example 2

Breeding of the Rice Giant of the Present Invention

The seeds of Koshihikari (recurrent parent) and Kasalath (donor parent) were provided, and first subjected to hastening of germination before cultivation in a greenhouse and earing for crossing. The crossing was carried out with Koshihikari as a female plant and Kasalath as a male plant, and the female plant is castrated prior to pollination. After the crossing procedure, the plant was ripened to get the seeds of the first filial generation F1.

The seeds of the first filial generation F1 were cultivated for earing, whereupon Koshihikari was crossed therewith and backcrossed to get the BC1F1 generation. The crossing in this stage was carried out with the first filial generation F1 as a female plant and Koshihikari as a male plant.

As regards the seeds of the BC1F1 generation thus obtained, backcrossing was repeated further twice with the BC1F1 generation as a female plant and Koshihikari as a male plant to get a BC3F1 generation.

Next, the genotypes of the chromosomes of the BC3F1 generation thus obtained were typed with SNP markers.

In the typing of the genotype, the seeds of the generation to be typed were sowed, the leaves of seedlings were collected about 7 to 14 days after sowing, and the genomic DNA was extracted from the leaves by the simple genome extraction method (Lisa Monna, et al., DNA Research, 9, 11-17, 2002).

First, the region containing SNPs is amplified by PCR with the genomic DNAs from the both lines, and after the confirmation of amplification by agarose gel electrophoresis, the amplified products are treated with enzymes to decompose the remaining primers and dephosphorylate mononucleotides. Next, the SNP primers constructed at single base prior to the SNPs and two fluorescence labeled dideoxynucleotides (two of ddATP, ddCTP, ddGTP and ddCTP) corresponding to the respective SNPs are subjected to the single base extension reaction with a PCR product as a template (AcycloPrime reaction). The reaction product exhibits a fluorescence polarization degree corresponding to the respective SNPs (Chen, X. et al., Genome Res., 9, 492-498, 1999), and thus the fluorescence polarization degree is measured for the typing of genotype.

An individual plant in which SNP-4 and SNP-5 on the chromosome are of the Kasalath type and 80% or more of the remaining SNP sites are of the Koshihikari type was selected on the basis of the typing.

The selected BC3F1 generation was inbred to get a BC4F1 generation, of which the genotypes of the chromosomes were typed, and an individual plant in which only SNP-4 and SNP-5 on the chromosome were of the Kasalath type or only SNP-4 and SNP-5 and SNP-3 and/or SNP-6 as the vicinity thereof were of the Kasalath type was selected.

The selected BC3F1 generation was inbred to get a BC4F2 generation, and was subjected to raising of seedlings with 1000 individual plants, and the ones, in which SNP-101, SNP-102, SNP-104 and SNP-105 exhibit the genotypes of Koshihikari-homotype, heterotype, heterotype and heterotype, or heterotype, heterotype, heterotype and Koshihikari-homotype, respectively, are selected from among these individual plants.

Next, the selected BC3F2 generation was inbred to get a BC4F3 generation, and was subjected to raising of seedlings with 1000 individual plants, and the ones, in which SNP-101, SNP-102, SNP-104 and SNP-105 exhibited the genotypes of Koshihikari-homotype, heterotype, heterotype and Koshihikari-homotype, respectively, were selected from among these individual plants.

The further selected BC4F3 generation was inbred to get a BC4F4 generation, and was subjected to raising of seedlings with 20 individual plants. The individual plants, in which SNP-101, SNP-102, SNP-104 and SNP-105 exhibited the genotypes of Koshihikari-homotype, Kasalath-homotype, Kasalath-homotype and Koshihikari-homotype, respectively, were selected from among these individual plants by typing.

The target rice plant was obtained by these selection procedures. In this connection, the rice plant obtained according to the present invention had a displacement rate into the Koshihikari type of 99.9%.

Example 3

Cultivation Test

The fixed line obtained according to the procedures in Example 2 was cultivated twice in the field (farm in Togo-cho, Aichi-gun, Aichi-pref., Japan) over the two years of 2005 and 2006 for detailed character examination (characteristic examination).

In the character examination, the varieties of Koshihikari and Nipponbare were cultivated as comparative examples under the same condition.

The scale of cultivation was 0.06 acre, and field husbandry was carried out according to the standard field husbandry method of paddy rice in Aichi prefecture. The rice plant according to the present invention had no resistance to disease damage in common with Koshihikari, and thus chemicals required were sprayed for control at appropriate seasons.

Example 4

Characteristics of the Rice Plant According to the Present Invention

The rice plant according to the present invention which was cultivated according to the procedures in Example 3 and Koshihikari and Nipponbare as the comparative examples were compared by measuring their culm lengths, ear lengths, numbers of ears, weights of 1000 grains, weights of 1000 decorticated grains, and redifferentiation capacities of seeds. Measurement and evaluation were carried out according to the examination standard and the table of characteristics published in the variety registration home page of the Ministry of Agriculture, Forestry and Fisheries. The results are shown below.

Figure 9:
FIG. 9 shows the photographs of the forms of the rice plant according to the present invention and Koshihikari at their heading times.
Figure 10:
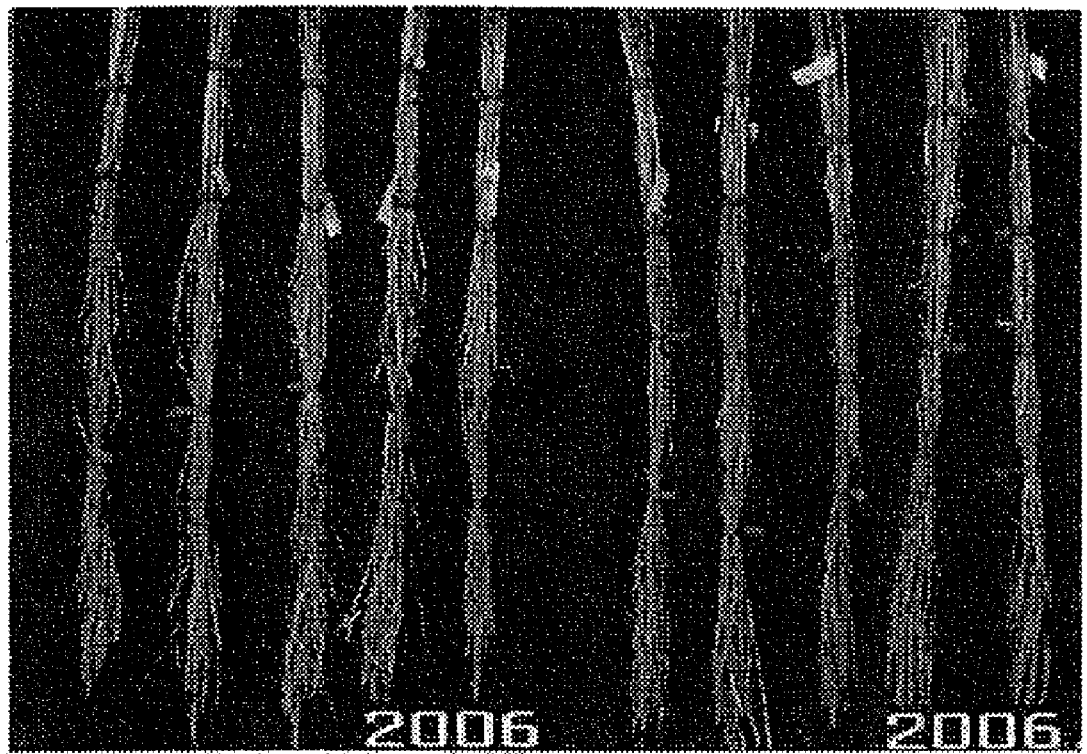
FIG. 10 shows the photographs of the harvested rice plants according to the present invention and of Koshihikari.
Figure 11:
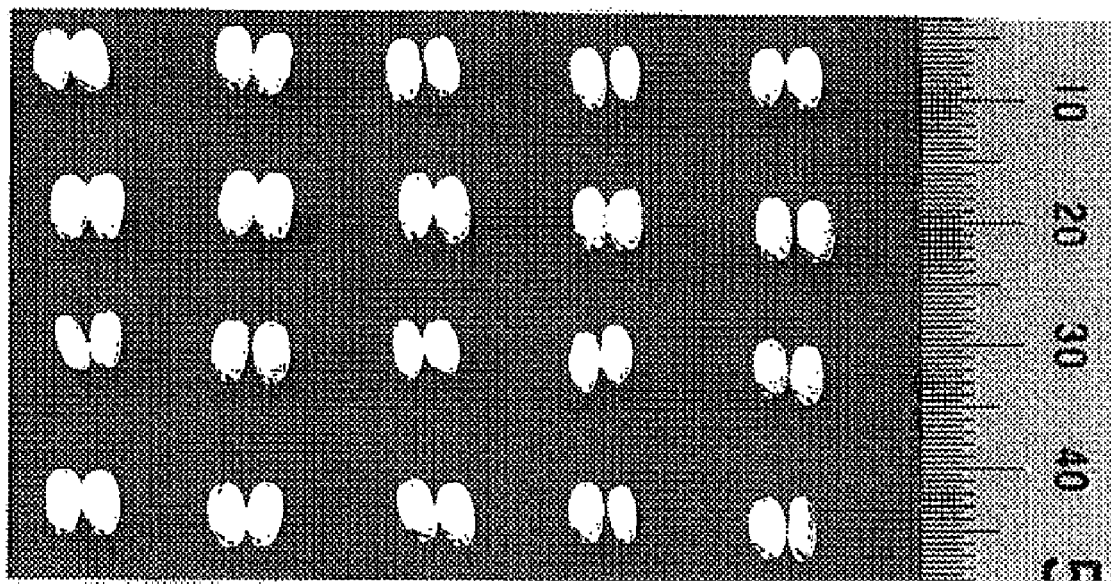
FIG. 11 shows the photograph of the decorticated grains of the rice plant according to the present invention and of Koshihikari, Nipponbare and Akihikari as the comparative examples.

In this connection, FIG. 9 shows the photographs of the forms of the rice plant according to the present invention and Koshihikari at their heading times. FIG. 10 shows the photographs of the harvested rice plants according to the present invention and of Koshihikari. Also, FIG. 11 shows the photograph of the decorticated grains of the rice plant according to the present invention and of Koshihikari, Nipponbare and Akihikari as the comparative examples.

Heading Time:

Heading time (heading date) was examined on the respective varieties. It has been confirmed that both the heading dates were almost indistinguishable between the rice plant according to the present invention (August 8 on both cultivations in 2005 and 2006) and Koshihikari (August 8 in 2005, and August 9 in 2006).

Culm Length:

Rice plants at the time of maturity were harvested, and each culm length excluding ear length was measured to obtain the mean culm length for each cultivation condition.

Figure 4:
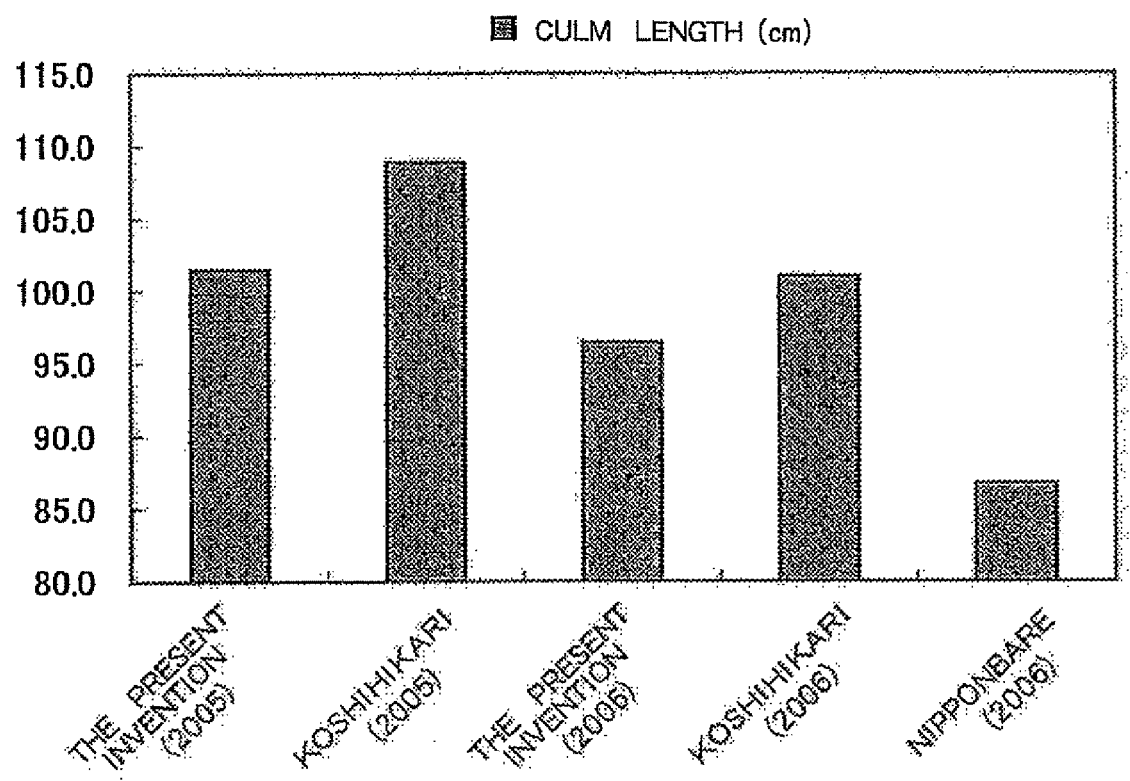
FIG. 4 shows the results of measuring the culm lengths of the cultivated varieties.

The results are shown in FIG. 4.

Apparently from the results, the rice plant according to the present invention at the time of maturity had a culm length about 6 cm shorter than Koshihikari on an average.

Figure 5:
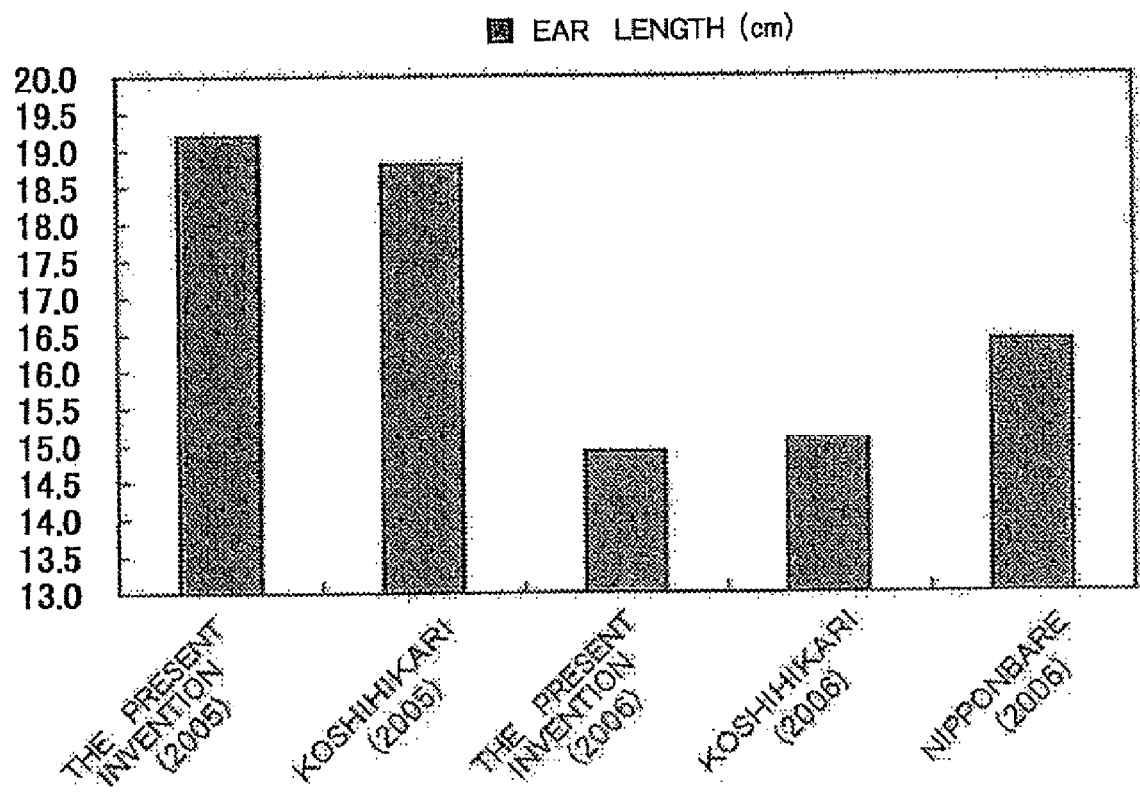
FIG. 5 shows the results of measuring the ear lengths of the cultivated varieties.
Figure 6:
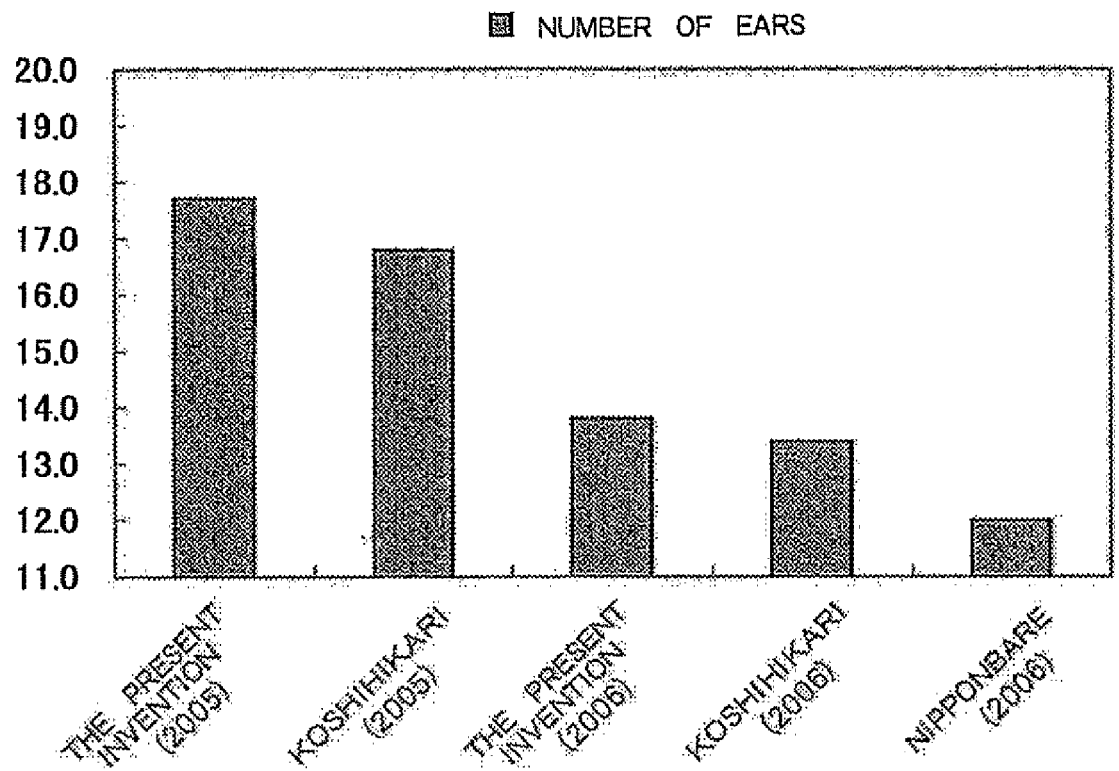
FIG. 6 shows the results of measuring the number of ears of the cultivated varieties.

Ear Length and Number of Ears:

The results on the ear length and number of ears of the rice plants are shown in FIGS. 5 and 6, respectively.

Figure 7:
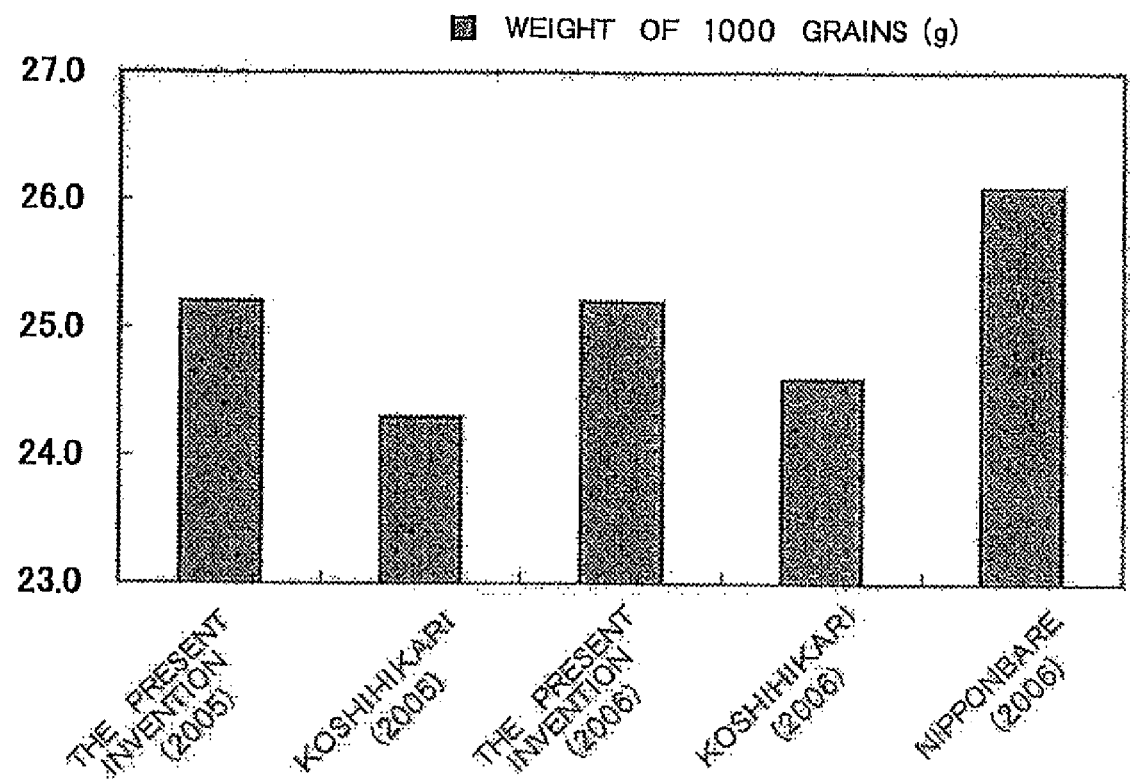
FIG. 7 shows the results of measuring the weight of 1000 grains of the cultivated varieties.

Weight of 1000 Grains:

The results are shown in FIG. 7

It has been observed that the rice plant according to the present invention tends to have the weight of 1000 grains larger than that of Koshihikari.

Figure 8:
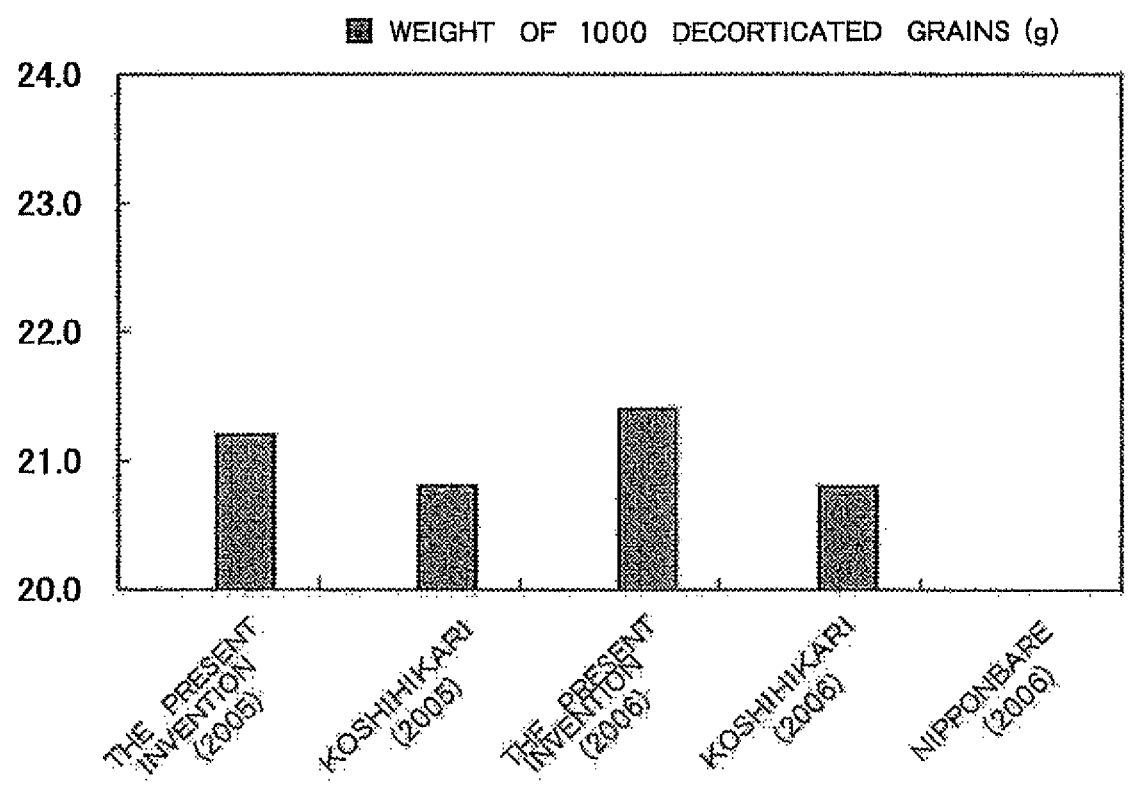
FIG. 8 shows the results of measuring the weight of 1000 decorticated grains of the cultivated varieties.

Weight of 1000 Decorticated Grains:

The results are shown in FIG. 8.

It has also been observed that the rice plant according to the present invention tends to have the weight of 1000 decorticated grains larger than that of Koshihikari.

Length, Width, Shape, Color and Aroma of Decorticated Grains:

The length of decorticated grain was 5.06 mm in the rice plant according to the present invention, while it was 5.01 mm in Koshihikari on an average of the measurements in 2005 and 2006.

The width of decorticated grain was 2.99 mm in the rice plant according to the present invention, while it was 2.91 mm in Koshihikari on an average of the measurements in 2005 and 2006.

The decorticated grain was semi-round in lateral view and light brown in color and had almost no aroma in both the rice plant according to the present invention and Koshihikari.

As described above, the rice plant according to the present invention had a culm length shorter than Koshihikari, and no significant difference was found in ear length and the other characteristics between these varieties. It may be thus concluded that the rice plant according to the present invention is superior to Koshihikari in lodging resistance.

Rice Taste Organoleptic Test:

The rice plant according to the present invention (lines 1 and 3) and Koshihikari (Comparative Example) (lines 2 and 4) were cultivated in the field of Example 3 under the same condition as above according to the conventional method. Ten individual rice plants of each line were harvested and sent to Japan Grain Inspection Association for taste organoleptic test.

In this connection, line 1 (the present invention) and line 2 (Comparative Example), and line 3 (the present invention) and line 4 (Comparative Example) were cultivated in the vicinal experimental plots.

In the rice taste sensory test, the test rice and the primary rice regulated by the Association (blended rice of Koshihikari and Nipponbare) were boiled under the same condition, and evaluated on the five items of appearance, aroma, taste, glutinousness and hardness of the test rice by 20 professional panelists to score plus for a good judgment and minus for a bad judgment in comparison with the primary rice. The scores were ranked as follows: 5: extremely; 4: very; 3: appreciably; 2: a little; 1: slightly.

According to these scores, each item was assessed with 11 ranks from −5 to +5 (7 ranks for glutinousness and hardness). Furthermore, the total assessment was calculated from the results of the five items according to the fixed method of the Association.

The results are shown in the following Table 3.

TABLE 3

| Test Sample | Appearance | Aroma | Taste | Glutinousness | Hardness | Total Assessment | | |
|---|---|---|---|---|---|---|---|---|
| | | | | | | Assessment | Confidence Interval | Significance |
| Line 1 (The present invention) | −0.900 | 0.100 | −0.300 | 0.250 | −0.250 | −0.350 | ±0.456 | 0 |
| Line 2 (Koshihikari, Comparative Example) | −0.450 | −0.050 | −0.250 | −0.200 | 0.150 | −0.350 | ±0.456 | 0 |
| Line 3 (The present invention) | −0.500 | 0.300 | 0.050 | 0.500 | −0.550 | 0.300 | ±0.306 | 0 |
| Line 4 (Koshihikari, Comparative Example) | 0.650 | 0.200 | 0.500 | 0.550 | −0.400 | 0.550 | ±0.306 | + |

Apparently from the results, there were no significant differences in the total assessment of eating qualities between the rice plant according to the present invention and Koshihikari which were cultivated in the vicinal experimental plots. Little difference was also observed in the other assessment items, and thus it has been believed that the rice plant according to the present invention had eating quality equal to Koshihikari.

What is claimed is:

1. A rice plant obtained by crossing of rice varieties "Koshihikari" with "Kasalath" and having improvement in both lodging resistance and decorticated grain size, wherein said rice plant has the nucleotide sequence of SEQ ID NO: 1 within the region between SNP-4 and SNP-5 on chromosome 1, and wherein the remaining region of the chromosome 1 is composed of chromosomes derived from Koshihikari.

2. The rice plant according to claim 1, which is a non-genetically modified plant.

3. A rice plant obtained by a method comprising the steps of:
   (a) crossing Koshihikari as the female plant with Kasalath as the male plant to develop a F1 hybrid (first filial generation),
   (b) backcrossing the F1 hybrid with Koshihikari followed by additional backcrossing of at least two times,
   (c) screening for the genotype of the region between SNP-4 and SNP-5 on the chromosome 1 of the generation, and
   (d) selecting the plant or progeny with respect to SNP-101, SNP-102, SNP-103, SNP-104 and SNP-105 which are plural SNP sites which are found between SNP-4 and SNP-5, in which SNP-101, SNP-102, SNP-104 and SNP-105 exhibit the genotypes of Koshihikari-homotype, Kasalath-homotype, Kasalath-homotype and Koshihikari-homotype, respectively, and in which the remaining sites exhibit the genotypes of Koshihikari-homotype wherein the plant exhibits improvement in both lodging resistance and decorticated grain size.

4. A method for cross-breeding a rice plant, in which the rice plant according to claim 1 is used as one of crossing parents.

5. A method for producing a rice plant variety having improvements in both lodging resistance and decorticated grain size, which comprises the steps of:
   (a) crossing Koshihikari as the female plant with Kasalath as the male plant to develop a F1 hybrid,
   (b) backcrossing the F1 hybrid with Koshihikari followed by additional backcrossing of at least two times,
   (c) screening for the genotype of the region between SNP-4 and SNP-5 on the chromosome 1 of the generation, and
   (d) selecting the plant or progeny with respect to SNP-101, SNP-102, SNP-103, SNP-104 and SNP-105 which are plural SNP sites which are found between SNP-4 and SNP-5, in which SNP-101, SNP-102, SNP-104 and SNP-105 exhibit the genotypes of Koshihikari-homotype, Kasalath-homotype, Kasalath-homotype and Koshihikari-homotype, respectively, and in which the remaining sites exhibit the genotypes of Koshihikari-homotype.

6. A method for cross-breeding a rice plant, in which the rice plant according to claim 3 is used as one of crossing parents.

* * * * *